US009494779B2

(12) United States Patent
Tanabe

(10) Patent No.: US 9,494,779 B2
(45) Date of Patent: Nov. 15, 2016

(54) OPTICAL ANALYSIS DEVICE, OPTICAL ANALYSIS METHOD AND COMPUTER PROGRAM FOR OPTICAL ANALYSIS USING SINGLE PARTICLE DETECTION

(71) Applicant: OLYMPUS CORPORATION, Tokyo (JP)

(72) Inventor: Tetsuya Tanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 168 days.

(21) Appl. No.: 14/451,021

(22) Filed: Aug. 4, 2014

(65) Prior Publication Data

US 2014/0339444 A1   Nov. 20, 2014

Related U.S. Application Data

(63) Continuation of application No. PCT/JP2013/052446, filed on Feb. 4, 2013.

(30) Foreign Application Priority Data

Feb. 17, 2012   (JP) ................................ 2012-032421

(51) Int. Cl.
    *G02B 21/00*   (2006.01)
    *G01N 21/64*   (2006.01)
    (Continued)

(52) U.S. Cl.
    CPC ....... *G02B 21/0084* (2013.01); *G01N 15/1429* (2013.01); *G01N 15/1434* (2013.01);
    (Continued)

(58) Field of Classification Search
    USPC ................ 356/335–339, 317–318; 250/573, 250/203.3, 206.1, 458.1, 459.1
    See application file for complete search history.

(56) References Cited

U.S. PATENT DOCUMENTS 4,251,733 A   2/1981   Hirleman, Jr.
5,866,336 A   2/1999   Nazarenko et al.
(Continued)

FOREIGN PATENT DOCUMENTS

EP   1 906 172 A1   4/2008
JP   04-337446 A    11/1992
(Continued)

OTHER PUBLICATIONS

English translation of Written Opinion by ISA of International Application No. PCT/JP2013/052446 (Form PCT/ISA/237) mailed Mar. 5, 2013 with ISR (Form PCT/ISA/210) (6 pages).
(Continued)

*Primary Examiner* — Sang Nguyen
(74) *Attorney, Agent, or Firm* — Westerman, Hattori, Daniels & Adrian, LLP

(57) ABSTRACT

In the optical analysis technique of detecting an existence of a single particle in a sample solution with a confocal microscope or a multiphoton microscope according to the scanning molecule counting method of the present invention, the position of a light detection region is moved in the sample solution; the light intensity from the light detection region is measured so that light intensity data will be generated; a first occurrence probability in assuming a first condition that no single particles exist in the light detection region and a second occurrence probability in assuming a second condition that a single particle exists in the light detection region for a time variation of light intensity value on the light intensity data are computed; and a signal indicating each single particle is detected based on those occurrence probabilities, and thereby enabling improvements in the sensitivity and/or S/N ratio.

20 Claims, 11 Drawing Sheets

(51) Int. Cl.
  *G01N 15/14* (2006.01)
  *G02B 21/16* (2006.01)
  *G01N 21/84* (2006.01)

(52) U.S. Cl.
  CPC ...... *G01N 21/6408* (2013.01); *G01N 21/6458* (2013.01); *G01N 21/6486* (2013.01); *G02B 21/0004* (2013.01); *G02B 21/0076* (2013.01); *G01N 2021/8405* (2013.01); *G01N 2201/12* (2013.01); *G02B 21/16* (2013.01)

(56) References Cited

U.S. PATENT DOCUMENTS

| | | |
|---|---|---|
| 6,280,960 B1 | 8/2001 | Carr |
| 6,376,843 B1 | 4/2002 | Palo |
| 6,388,746 B1 | 5/2002 | Eriksson et al. |
| 6,388,788 B1 | 5/2002 | Harris et al. |
| 6,400,487 B1 | 6/2002 | Harris et al. |
| 6,403,338 B1 | 6/2002 | Knapp et al. |
| 6,710,871 B1 | 3/2004 | Goix |
| 6,782,297 B2 | 8/2004 | Tabor |
| 6,856,391 B2 | 2/2005 | Garab et al. |
| 6,927,401 B1 | 8/2005 | Palo |
| 8,284,484 B2 | 10/2012 | Hoult et al. |
| 8,681,332 B2 | 3/2014 | Tanabe |
| 9,068,944 B2 | 6/2015 | Tanabe |
| 9,188,535 B2 | 11/2015 | Hanashi |
| 2001/0035954 A1 | 11/2001 | Rahn et al. |
| 2002/0008211 A1 | 1/2002 | Kask |
| 2002/0036775 A1 | 3/2002 | Wolleschensky et al. |
| 2003/0036855 A1 | 2/2003 | Harris et al. |
| 2003/0218746 A1 | 11/2003 | Sampas |
| 2004/0022684 A1 | 2/2004 | Heinze et al. |
| 2004/0051051 A1 | 3/2004 | Kato et al. |
| 2004/0150880 A1 | 8/2004 | Nakata et al. |
| 2005/0260660 A1 | 11/2005 | van Dongen et al. |
| 2006/0078998 A1 | 4/2006 | Puskas et al. |
| 2006/0158721 A1 | 7/2006 | Nakata et al. |
| 2006/0256338 A1 | 11/2006 | Gratton et al. |
| 2008/0052009 A1 | 2/2008 | Chiu et al. |
| 2009/0159812 A1 | 6/2009 | Livingston |
| 2009/0222218 A1 | 9/2009 | Chamberlin et al. |
| 2010/0033718 A1 | 2/2010 | Tanaami |
| 2010/0177190 A1 | 7/2010 | Chiang et al. |
| 2010/0202043 A1 | 8/2010 | Ujike |
| 2012/0319009 A1* | 12/2012 | Yamaguchi ........ G01N 15/1456 250/459.1 |
| 2013/0228705 A1 | 9/2013 | Nishikawa et al. |
| 2013/0302906 A1 | 11/2013 | Tanabe |
| 2013/0314705 A1 | 11/2013 | Tanabe et al. |
| 2014/0024020 A1* | 1/2014 | Tanabe ............... G01N 21/6408 435/5 |
| 2014/0134608 A1 | 5/2014 | Hanashi et al. |
| 2015/0108369 A1* | 4/2015 | Hanashi ............. G01N 15/1429 250/459.1 |

FOREIGN PATENT DOCUMENTS

| | | |
|---|---|---|
| JP | 10-512952 A | 12/1998 |
| JP | 2002-507762 A | 3/2002 |
| JP | 2002-543414 A | 12/2002 |
| JP | 2004-506192 A | 2/2004 |
| JP | 2005-098876 A | 4/2005 |
| JP | 2005-099662 A | 4/2005 |
| JP | 2007-020565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2010-017127 A | 1/2010 |
| JP | 2011-002415 A | 1/2011 |
| JP | 2011-508219 A | 3/2011 |
| JP | 2013-036765 A | 2/2013 |
| WO | 98/16814 A1 | 4/1998 |
| WO | 99/47963 A1 | 9/1999 |
| WO | 00/66985 A1 | 11/2000 |
| WO | 02/12864 A1 | 2/2002 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/117033 A2 | 9/2009 |
| WO | 2011/108369 A1 | 9/2011 |
| WO | 2011/108370 A1 | 9/2011 |
| WO | 2011/108371 A1 | 9/2011 |
| WO | 2012/050011 A1 | 4/2012 |
| WO | 2012/099234 A1 | 7/2012 |
| WO | 2013/069504 A1 | 5/2013 |
| WO | 2013/121905 A1 | 8/2013 |

OTHER PUBLICATIONS

Park, Mira et al., "Counting the Number of Fluorophores Labeled in Biomolecules by Observing the Fluorescence-Intensity Transient of a Single Molecule" Bulletin of the Chemical Society of Japan, dated Aug. 30, 2005, vol. 78, No. 9, p. 1612-1618.
U.S. Office Action dated Apr. 2, 2013, issued in related U.S. Appl. No. 13/596,280.
Kask, Peet et al., "Two-Dimensional Fluorescence Intensity Distribution Analysis: Theory and Applications", Biophysical Journal, Apr. 2000, vol. 78, p. 1703-1713.
Chinese Office Action dated Aug. 13, 2013, issued in related Chinese application No. 2011800116553; w/ English Translation (16 pages).
International Search Report dated Mar. 29, 2011, issued in related PCT/JP2011/053483.
International Preliminary Report on Patentability (PCT/IPEA/409) issued in related PCT/JP2011/053483.
Chinese Office Action dated Aug. 9, 2013, issued in related Chinese application No. 2011800116407; w/ English Translation (16 pages).
International Search Report Mar. 29, 2011, issued in related PCT/JP2011/053482.
International Preliminary Report on Patentability (PCT/IPEA/409) issued in related PCT/JP2011/053482.
U.S. Office Action dated Jan. 3, 2013, issued in related U.S. Appl. No. 13/597,825.
Chinese Office Action dated Feb. 7, 2013, issued in related Chinese application No. 201180011644.5; w/ English Translation (18 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) issued in related PCT/JP2011/053481.
Goodwin, Peter et al., "Rapid Sizing of Individual Fluorescently Stained DNA Fragments by Flow Cytometry," Nucleic Acids Research, 1993, vol. 21, No. 4, p. 803-806.
Keller, Richard et al., "Single-Molecule Fluorescence Analysis in Solution," Applied Spectroscopy, 1996, vol. 50, No. 7, p. 12A-32A.
Lee, Yuan-Hsiang et al., "Laser-Induced Fluorescence Detection of a Single Molecule in a Capillary," Analytical Chemistry, dated Dec. 1, 1994, vol. 66, No. 23, p. 4142-4149.
Li, Haitao et al., "Ultrasensitive Coincidence Fluorescence Detection of Single DNA Molecules," Analytical Chemistry, dated Apr. 1, 2003, vol. 75, No. 7, p. 1664-1670.
Nie, Shuming et al., "Probing Individual Molecules with Confocal Fluorescence Microscopy," Science, dated Nov. 11, 1994, vol. 266, p. 1018-1021.
Tahari, Abdel. "Fluorescence Correlation Spectroscopy: Ultrasensitive Detection in Clear and Turbid Media," University of Illinois, 2006, p. 1-88.

(56) References Cited

OTHER PUBLICATIONS

Wu, Alan et al., "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, p. 2157-2159.
Itoh et al., "A New Method for Detection of Influenza Viruses by Single Particle-Recognition Based on the Principle of Fluorescence Correlation Spectroscopy," Chemistry and Biology, 2009, vol. 47, No. 12, p. 823-830.
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.
U.S. Office Action dated Oct. 4, 2013, issued in related U.S. Appl. No. 13/596,243.
Japanese Office Action dated Dec. 18, 2012 issued in related JP application No. 2012-503060; w/ English Translation (6 pages).
Kinjo, M. "Single Molecule Detection by Fluorescence Correlation Spectroscopy", Proteins, Nucleic Acids and Enzymes, 1999, vol. 44, No. 9, p. 1431-1438.
Guo, Xiang-Qun et al., "Use of a Long-Lifetime Re(I) Complex in Fluorescence Polarization Immunoassays of High-Molecular-Weight Analytes", Analytical Chemistry, Feb. 1998, vol. 7, No. 3, p. 632-637.
Meyer-Almes, F. J. "A New Method for Use in Molecular Diagnostics and High Throughput Pharmaceutical Screening based on Fluorescence Correlation Spectroscopy", Nanoparticle Immunoassays, R. Ridger, edit, Springer, Berlin, 2000, p. 204-224.
Kato, N. et al., "A Single Molecule Analyzer that Enables New Analysis of DNA and Protein Interactions", Gene Medicine, 2002, vol. 6, No. 2, p. 271-277.
International Search Report dated Mar. 5, 2013, issued in related PCT/JP2013/052446.
Kask, P. et al., "Fluorescence-intensity Distribution Analysis and its Application in Biomolecular Detection Technology", PNAS, vol. 96, No. 24, 1999, p. 13756-13761.
Petrasek et al. "Circular scanning fluorescence correlation spectroscopy on membranes" Optics Express, Dec. 5, 2011, vol. 19, No. 25, pp. 25006-25021, cited in Extended European Search Report dated Aug. 24, 2015.
Foldes-Papp et al. "A new concept for ultrasensitive fluorescence measurements of molecules in solution and membrane: 1. Theory and a first application" Journal of Immunological Methods, Amsterdam, NL, Mar. 2004, vol. 286, No. 1-2, (pp. 1-11), cited in Extended European Search Report dated Aug. 24, 2015.
Extended European Search Report dated Aug. 24, 2015, issued in EP Application No. 13748583.5. (7 pages).
Final Office Action dated Sep. 28, 2015, issued in U.S. Appl. No. 13/749,968 (24 pages).
Final Office Action dated Sep. 29, 2015, issued in U.S. Appl. No. 13/946,091 (23 pages).
International Search Report dated Sep. 22, 2014, issued in related International Application No. PCT/JP2014/067339 with forms PCT/ISA/220 and PCT/ISA/237 (9 pages).
Extended European Search Report dated Oct. 20, 2014, issued in related EP Application No. 12770835.2 (10 pages).
Translation of Written Opinion dated Sep. 22, 2014, issued in counterpart International Application No. PCT/JP2014/067339. (5 pages).
Related co-pending U.S. Appl. No. 15/084,246.
Non-final Office Action dated Jul. 14, 2016 issued in co-pending U.S. Appl. No. 15/084,246.

\* cited by examiner

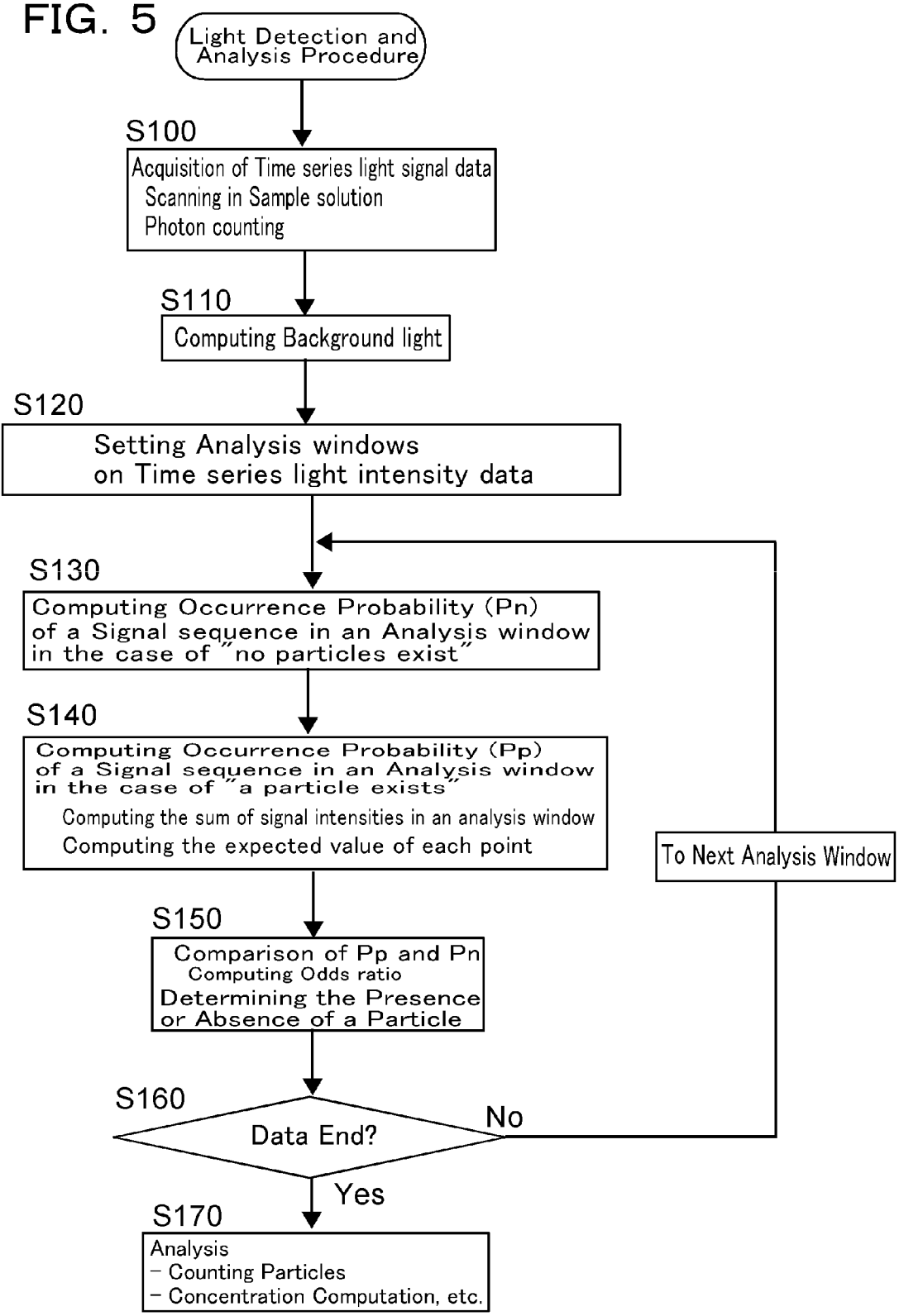

FIG. 10
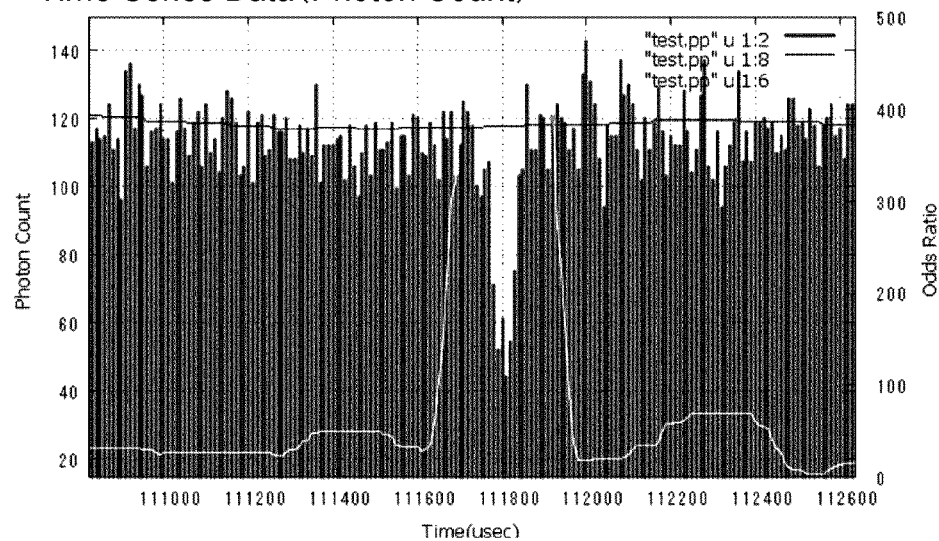
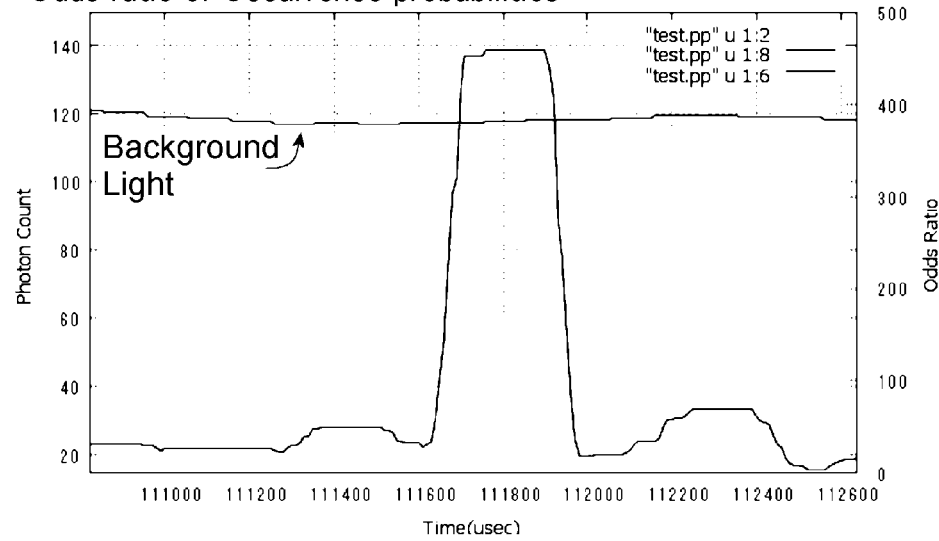

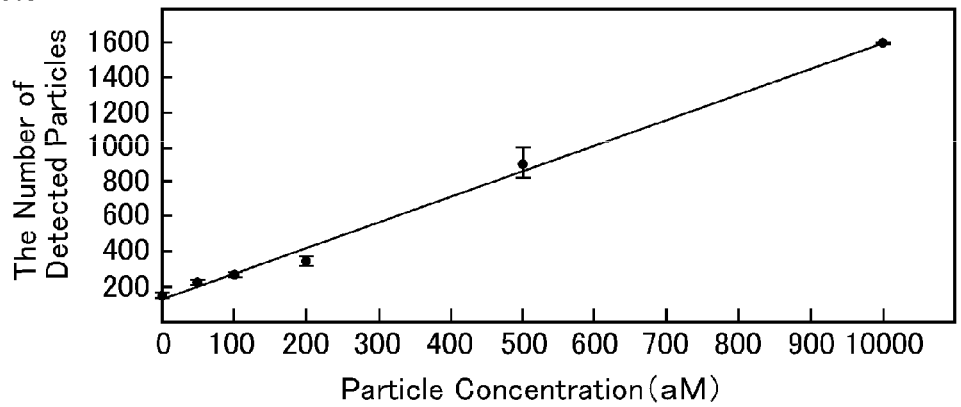
FIG. 11A Particle Detection Based On Occurrence Probabilities (The Present Invention)
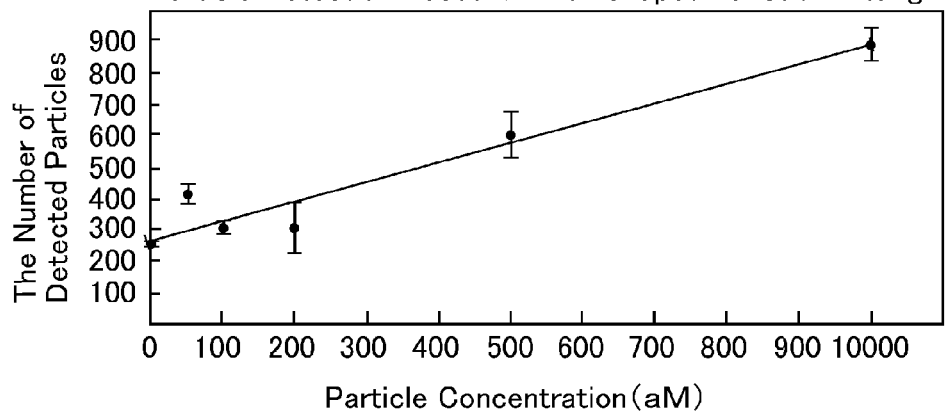
FIG. 11B Particle Detection Based On Bell Shaped Function Fitting
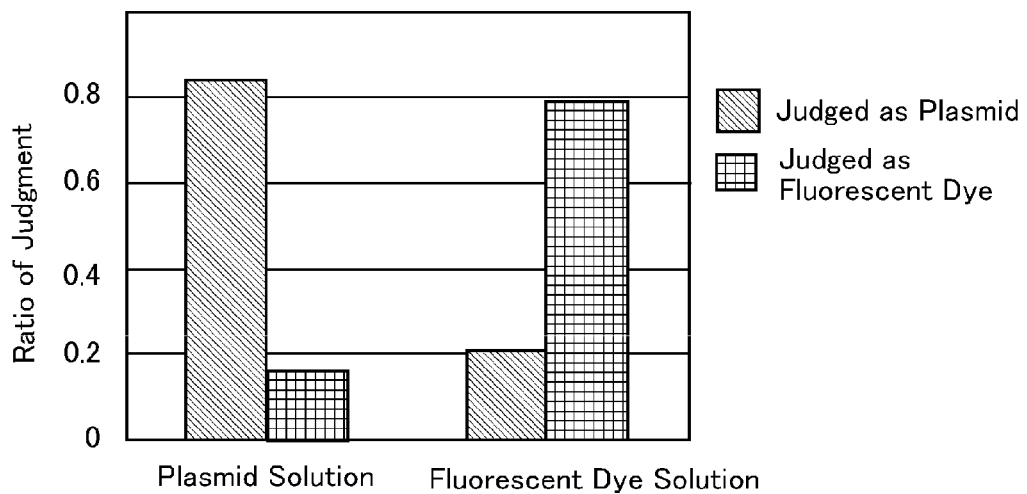
FIG. 12

OPTICAL ANALYSIS DEVICE, OPTICAL ANALYSIS METHOD AND COMPUTER PROGRAM FOR OPTICAL ANALYSIS USING SINGLE PARTICLE DETECTION

TECHNICAL FIELD

This invention relates to an optical analysis technique capable of detecting a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to an optical analysis device, optical analysis method and computer program for optical analysis, which detect individually a variation of light because of an existence of a single particle (the light emitted by a single particle or the shadow generated by a single particle), using an optical system as described above, to make it possible to conduct various optical analyses. In this regard, in this specification, the light to be detected may be fluorescence, phosphorescence, chemiluminescence, bioluminescence, scattered light, etc. The particle which emits light (hereafter, referred to as a "light-emitting particle") may be any of particles which emit light by themselves and particles to which an arbitrary light-emitting label or light-emitting probe has been attached.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed optical analysis techniques of performing detection of a characteristic, an intermolecular interaction, a binding or dissociating reaction of a biological molecule, etc. by means of such a faint light measurement technique. As such optical analysis techniques, for example, there are known Fluorescence Correlation Spectroscopy (FCS, see e.g. patent documents 1-3 and non-patent documents 1-3), Fluorescence Intensity Distribution Analysis (FIDA, e.g. patent document 4, non-patent document 4) and Photon Counting Histogram (PCH, e.g. patent document 5). In addition, in patent documents 6-8, there are proposed methods of detecting fluorescent substances based on a time progress of fluorescence signals of a sample solution measured using the optical system of a confocal microscope.

Furthermore, in patent documents 9-11, Applicant of the present application has proposed a novel optical analysis technique, using an optical system which is capable of detecting the light from a micro region in a solution, such as an optical system of a confocal microscope or a multiphoton microscope, and employing a different principle from optical analysis techniques, such as FCS and FIDA. In the case of optical analysis techniques, such as the above-mentioned FCS, FIDA, the light intensity data obtained by continuously measuring lights from fluorescence molecules floating in a micro region, in which light is detected, in a sample solution (hereafter, called a "light detection region") is analyzed through calculation processing which computes statistical fluctuations, and thereby a concentration and/or other characteristics of fluorescence molecules are detected. On the other hand, in the new optical analysis technique proposed in patent documents 9-11, the position of a light detection region is moved in a sample solution (i.e., the inside of the sample solution is scanned with the light detection region), and when the light detection region encompasses a light-emitting particle being dispersed and moving at random in the sample solution, the light emitted from the light-emitting particle is individually detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called the "scanning molecule counting method", hereafter.), not only the sample amount necessary for measurement may be very small (for example, about several 10 μL) and the measuring time is short similarly to optical analysis techniques, such as FCS and FIDA, but also, it becomes possible to detect the presence of a light-emitting particle and quantitatively detect its characteristic, such as a concentration, a number density, etc., at a lower concentration or number density, as compared with the cases of optical analysis techniques, such as FCS and FIDA.

Thus, the "scanning molecule counting method" is expected to be a strong tool enabling an experiment or a test at low cost and/or more quickly than conventional biochemical methods, and also enabling the detection of a concentration and/or a characteristic of a particle of a lower concentration at which FCS, FIDA, etc. cannot be acceptably performed, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446
Patent document 9: WO2011/108369
Patent document 10: WO2011/08370
Patent document 11: WO2011/108371

Non-Patent Documents

Non-patent document 1: Masataka Kinjo; "Protein, Nucleic acid, Enzyme" Vol. 44. No. 9, pages 1431-1438, 1999.

Non-patent document 2: F. J. Meyer-Alms; "Fluorescence Correlation Spectroscopy" edt. R. Rigler, Springer. Berlin, pages 204-224, 2000.

Non-patent document 3: Noriko Kato, et al. "Gene medicine". Vol. 6, No. 2, pages 271-277.

Non-patent document 4: P. Kask, K. Palo, D. Ullmann, K. Gall PNAS 96, 13756-13761 (1999)

Non-patent document 6: Anal. Chem. Vol. 70 No. 3 632 page. 1998

SUMMARY OF INVENTION

Technical Problem

In the scanning molecule counting method described in the above-mentioned patent documents 9-11, typically, under an assumption that a bell shaped variation of the light intensity in time series data of the light intensity from a light detection region (time series light intensity data) corresponds to the existence of a single particle to be an observation object, the detection of such a bell shaped variation of light intensity is performed. For instance, in a case that a particle to be observed is a light-emitting particle (as described later, a particle to be observed can be a particle which emits no light in a detected wavelength band (non-light-emitting particle)), among bell shaped or pulse form light intensity increases observed in time series light intensity data, a light intensity variation whose conditions are consistent with the profile of a light intensity increase (the peak intensity, full width at half maximum, etc.) expected in a light-emitting particle passing through the inside of a light detection region is detected as a signal indicating the existence of a particle. On the other hand, a light intensity increase which does not satisfy the conditions of the profile of a light intensity increase of a light-emitting particle is judged as a noise.

However, in the case of detecting a bell shaped signal as described above in time series light intensity data, it will be difficult to discriminate between a particle signal and a noise signal if the magnitude of the particle signal becomes weak.

As explained more in detail in the column of embodiments described later, in order to catch the weak light intensity from a particle to be observed or its variation, light intensity measurement is typically performed by the photon counting, and thus the time series light intensity data becomes discrete photon counting data (see FIG. 2A). In that case, for making detection of a bell shaped signal easier, preferably, time series light intensity data is smoothed in time, and a bell shaped signal which satisfies the profile condition of the light intensity variation of a particle is detected in the smoothed time series light intensity data. However, in this manner, when the intensity variation of a signal of a particle is small, such a signal is buried in noises in the stage of the photon counting data, and does not exhibits the characteristics of a bell shaped profile of the intensity variation of a signal of a particle even after the smoothing process, so that it cannot be detected as a signal of a particle. Especially, the magnitude of a signal corresponding to the existence of a particle varies depending upon the passing route of the particle in the inside of the light detection region, where the intensity variation of a signal of a particle passing through the circumference part of the light detection region is small. Thus, many weak signals of particles passing through the circumference part of the light detection region are overlooked or a noise signal is erroneously judged as a weak particle signal, and this has been one of the hindrances against improvements in the sensitivity or accuracy of the scanning molecule counting method.

Thus, the main object of the present invention is to provide a new technique or way of detecting a particle signal which enables further improvement in the sensitivity and/or accuracy in the above-mentioned scanning molecule counting method.

Further, another object of the present invention is to provide a new technique or way of detecting a particle signal which enables more accurate discrimination between a weak particle signal and a noise signal in the above-mentioned scanning molecule counting method.

With respect to the above-mentioned objects, the inventor of the present invention has found that, in time series light intensity data of the scanning molecule counting method, there is a difference in occurrence patterns of the time variation of light intensity (photon count sequence) between the portion corresponding to a signal of a particle and the portion of a noise signal. Namely, photons of noise signals are always detected at random, while photons of particle signals are detected concentratively in time. In the present invention, with a new algorithm which can detect the difference in the occurrence patterns of the time variation of light intensity, an improvement in the detection precision of a signal of a particle in the scanning molecule counting method will be achieved. Further, since the occurrence pattern of the time variation of light intensity also changes with characteristics of particles (such as polarization characteristics, emission wavelength characteristics), discrimination of particles of different characteristics is also tried based on the difference in the occurrence patterns of the time variation of light intensity.

Solution to Problem

Thus, according to the present invention, the above-mentioned object is achieved by an optical analysis device which detects a single particle dispersed and moving at random in a sample solution using an optical system of a confocal microscope or a multiphoton microscope, comprising: a light detection region mover which moves a position of a light detection region of the optical system of the microscope in the sample solution; a light detector which detects light from the light detection region; and a signal processor which generates time series light intensity data of the light from the light detection region detected with the light detector during the moving of the position of the light detection region in the sample solution and detects a signal indicating an existence of each single particle individually in the time series light intensity data; wherein the signal processor computes a first occurrence probability in assuming a first condition that no single particles exist in the light detection region and a second occurrence probability in assuming a second condition that a single particle exists in the light detection region for a time variation of light intensity value in each analysis window set out in time series on the time series light intensity data; and detects a signal indicating an existence of each single particle on the time series light intensity data based on the first and second occurrence probabilities.

In the structure of the above-mentioned present invention, "a single particle dispersed and moving at random in a sample solution" may be a particle, such as an atom, a molecule or an aggregate of these, which is dispersed or dissolved in a sample solution, and it may be an arbitrary particulate matter making the Brownian motion freely in a solution without being fixed on a substrate, etc. The single particle to be an observation object may be a particle which emits light (light-emitting particle), or may be a particle which emits no light (in a detected wavelength band) (non-light-emitting particle). In a case that a particle to be observed is a light-emitting particle. "a signal indicating an existence of each single particle" becomes "a temporary increase of the light intensity value" on the time series light intensity data corresponding to light which a light-emitting particle emits during its passing through the inside of the light detection region. The light-emitting particle is typically a fluorescent particle, but may be a particle which emits light by phosphorescence, chemiluminescence, bioluminescence, light scattering, etc. A particle to be observed may also be a non-light-emitting particle, and in that case, the light from the light detection region includes a significant background light, and "a signal indicating an existence of each single particle" becomes a temporary reduction of the light intensity from the background light (the inverted scanning molecule counting method). In this regard, the "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the positional relationship between an objective and a pinhole. For a light-emitting particle which emits light without illumination light, for example, a molecule which emits light according to chemiluminescence or bioluminescence, no illumination light is required in the microscope.). Further, typically, the light detector detects the light from the light detection region by the photon counting in which (a) photon(s) arriving in every predetermined measuring unit time (bin time) is/are counted, and in that case, the time series light intensity data becomes time series photon count data.

As understood from the above, in the inventive device, basically, similarly to the "scanning molecule counting method" described in the patent documents 9-11, while moving the position of the light detection region in the sample solution, namely, while scanning the inside of the sample solution with the light detection region, the detection of light and the generation of the time series light intensity data indicating time series light intensity values are sequentially performed and a signal indicating the existence of a single particle is detected on the time series light intensity data. In this detection of a signal indicating the existence of a single particle, in the present invention, instead of detecting a signal of a single particle only based on whether or not the amount of increase or decrease of the light intensity value has exceeded beyond a predetermined amount, it is tested, in time series, in which of a case where a single particle exists in the light detection region and a case where no single particles exist in the light detection region the pattern of a time variation of light intensity value on the time series light intensity data is a pattern which is prone to be generated. That is, as already noted, in time series light intensity data, there is a difference in occurrence patterns of time variations of light intensity between a portion corresponding to a particle signal and a portion corresponding to a noise signal, and therefore, if the pattern of the time variation of the light intensity value in a certain portion on time series light intensity data is a pattern which is prone to be generated when no single particles exist in the light detection region, the portion can be judged as a portion including only noise signals, and if it is a pattern which is prone to be generated when a single particle exists in the light detection region, the portion can be judged as a portion corresponding to a particle signal. And, it can be judged whether a certain pattern of a time variation of light intensity value is a pattern which is prone to be generated in a case where a single particle exists in the light detection region or in a case where no single particle exists in the light detection region, according to the respective probabilities that that pattern of the time variation of light intensity value is generated in the case where a single particle exists in the light detection region and in the case where no single particle exists in the light detection region.

Thus, in the inventive device, in order to detect a portion in which a particle was present, i.e., an a signal indicating the existence of a single particle, on time series light intensity data, there are computed "a first occurrence probability in assuming a first condition that no single particles exist in the light detection region and a second occurrence probability in assuming a second condition that a single particle exists in the light detection region for a time variation of light intensity value in each analysis window set out in time series on the time series light intensity data". Here, an "analysis window" is a region of an arbitrary time width on the time series light intensity data, and the "analysis windows" are set sequentially or in time series on the time series light intensity data. In addition, "a first occurrence probability" is a probability that a time variation of light intensity measured in an "analysis window" would occur when no single particles exist in the light detection region, and "a second occurrence probability" is a probability that a time variation of light intensity measured in an "analysis window" would occur when a single particle exists in the light detection region. Then, since the "second occurrence probability" will becomes relatively larger than the "first occurrence probability" if a single particle exists in the light detection region, a time region in which a single particle exists in the light detection region is determined on the time series light intensity data by referring to the "first occurrence probability" and the "second occurrence probability", and thereby the detection of a signal indicating the existence of each single particle becomes possible.

In this regard, in the above-mentioned structure, the width of the analysis window may be set as an arbitrary width, for example, longer than the time taken for a single particle to pass through a light detection region. In addition, the analysis window may be set in every unit time or every predetermined time interval on the time series light intensity data (In this case, the analysis windows set in time series overlap mutually.), or may be set by dividing the time series light intensity data by a predetermined time width. The "unit time" is the time of the width which gives one light intensity value in optical measurement, and in a case of the photon counting, it may be the time of the width corresponding to one or more bin time(s).

In the above-mentioned structure, the first and second occurrence probabilities can be determined based upon the deviation of a pattern of a time variation of actually measured light intensity value from an average pattern of time variations of light intensity value when the first and second conditions are assumed in an analysis window, respectively. As the deviation of the pattern of the actual measured value from the average pattern becomes smaller, the probability of the occurrence of the pattern of the actual measurement becomes higher. Thus, the first and second occurrence probabilities can be computed out based upon the light intensity value detected in each unit time and an expected value in each unit time in assuming the first and second conditions in an analysis window, respectively. Moreover, the light intensity value appearing on the time series light intensity data is the photon count emitted from the inside of the light detection region or an amount proportional thereto, and therefore, it is considered that the light intensity value in each unit time follows the Poisson distribution. Then, in the above-mentioned structure, preferably, while it is assumed that the light intensity value in each unit time follows the Poisson distribution having the expected value in each unit time, a unit time occurrence probability of light intensity value in each unit time is computed, and the first and second occurrence probabilities each may be computed using the corresponding unit time occurrence probabilities, respectively.

Thus, in the above-mentioned device, in a simple case, it may be judged that a single particle has existed in the light detection region in the time of the analysis window in which the second occurrence probability is larger than the first occurrence probability. Further, the time when a single particle existed in the light detection region may be determined based upon the ratio or odds ratio of the first and second occurrence probabilities computed in time series.

By the way, in the above-mentioned scanning molecule counting method, it is possible to detect separately at least two mutually different components of the light from the light detection region and generate time series light intensity data of each of the components. In that case, it is possible to choose components to be detected so that an arbitrary characteristic of a single particle will be reflected in the data of the detected components. For instance, when components of which polarization directions are mutually different are selected as two or more components to be detected, the polarization characteristic of a particle will be reflected in the time series light intensity data of the two or more components. Further, when the light components of mutually different wavelength bands are selected as two or more components to be detected, the emission wavelength characteristic of a particle is reflected in the time series light intensity data of the two or more components. And, also in the patterns of time variation of light intensity value in the time series light intensity data of the two or more components, the characteristic of a particle to be observed as described above will be reflected.

Then, the above-mentioned inventive device may also be designed such that the light detector can separately detects at least two mutually different components of the light from the light detection region; the signal processor generates time series light intensity data of each of said components; and the signal processor can compute the first and second occurrence probabilities of each of the components. In this structure, through appropriately selecting components to be detected, it becomes possible to reflect in the second occurrence probability of each of the components of the detected light a predetermined characteristic value which a single particle to be an observation object possesses, namely to render the second occurrence probability to be a function of the predetermined characteristic value which the single particle possesses. And, by referring to the first and second occurrence probabilities for each of the components, it can be judged that a particle possessing the predetermined characteristic value has existed in a region in which the second occurrence probability, which is a function of the predetermined characteristic value, is relatively high (When a particle which does not have a predetermined characteristic value exists, the second occurrence probability, which is a function of the predetermined characteristic value, becomes low.). Namely, by using the first and second occurrence probabilities for each of the components, not only the presence or absence of the existence of a particle in the light detection region but also a time when a particle possessing a predetermined characteristic value exists in the light detection region on the time series light intensity data will be determined, and thus, it becomes possible to detect an existence of a particle possessing a predetermined characteristic value.

Furthermore, according to the manner using the first and second occurrence probabilities of each of at least two mutually different components as described above, in a case that single particles of two or more kinds possessing mutually different predetermined characteristic values are included as single particles, a time when a particle exists can be determined on time series light intensity data for each kind of single particle. Namely, through computing, for each kind of single particle, the second occurrence probability of each of the components, which is a function of those mutually different predetermined characteristic values (Since no particles exist in the first condition, the characteristic value of a particle is not reflected in the first occurrence probability.), and referring to the first occurrence probability of each of two or more components and the second occurrence probability of each of the components for each of the single particles of two or more kinds, it can be estimated that a particle of the kind which gives a relatively high value of the second occurrence probability exists in the light detection region. Thus, in a case that single particles include single particles of two or more kinds possessing mutually different predetermined characteristic values, the above-mentioned inventive device may be designed to compute by the kind of single particle the second occurrence probability of each of the components, which is a function of the mutually different predetermined characteristic values, and detect a signal indicating an existence of a single particle by the kind of single particle on the time series light intensity data based on the first occurrence probability of each of the components and the second occurrence probability of each of the components for each of the two or more kinds of single particle. In short, according to this structure, in a case that two or more kinds of single particle are contained in the sample solution, the detection of a particle becomes possible with identifying its kind.

In this regard, the characteristic value of a particle to be made to be reflected in the above-mentioned second occurrence probability, as noted, may be an index value indicating the polarization characteristics of a single particle, such as fluorescence anisotropy, and the emission wavelength characteristic of a single particle, such as the ratio of emitted light intensities in mutually different emission wavelength bands, etc.

The moving speed of the position of the light detection region in a sample solution in the above-mentioned inventive device may be changeable appropriately based on the characteristics, number density or concentration in the sample solution of a single particle to be observed. When the moving speed of the light detection region becomes higher, in a case that a single particle is a light-emitting particle, the light amount obtained from one light-emitting particle will be reduced, and in a case that a single particle is a non-light-emitting particle, the reduction amount of the light intensity value owing to the existence of one non-light-emitting particle becomes smaller. Therefore, it is preferable that the moving speed of the light detection region can be appropriately changed so that the variation of the light intensity value by a single particle can be measured precisely or with sufficient sensitivity. Moreover, the moving speed of the position of the light detection region in the sample solution is preferably set to be higher than the diffusional moving velocity of a single particle to be an object to be detected (the average moving speed of a particle owing to the Brownian motion). As explained above, in the inventive device, a pattern of a time variation of detected light intensity value is evaluated by using the (first and second) occurrence probabilities of the time variation pattern computed with assuming a case where a particle exists and a case where no particles exist in the light detection region (the first and second conditions), and thus, if it is taken into account that a particle moves also by the Brownian motion during its passing through the inside of the light detection region, the computation of the second occurrence probability will become complicated. Therefore, in the present invention, in order to make it possible to ignore the effect by the Brownian motion of a particle during its passing through the inside of the light detection region, it is preferable that the moving speed of the light detection region is set higher than the diffusion moving velocity of the single particle to be an object to be detected. In this regard, since the diffusional moving velocities differ depending upon single particles, it is preferable that the moving speed of the light detection region in the inventive device can be changed appropriately according to the characteristics (especially, the diffusion constant) of the particle as described above.

The moving of the position of the light detection region in a sample solution may be achieved by an arbitrary way. For example, the position of the light detection region may be changed by changing the optical path of the optical system of the microscope using a galvanometer mirror adopted in a laser scan type light microscope, or the position of the sample solution may be moved (e.g. by moving the stage of a microscope) so that the position of the light detection region will be moved in the sample solution. The movement track of the position of the light detection region may be set arbitrarily, for example, may be selected from circular, elliptical, rectangular, straight linear and curvilinear ones. Especially, in the case of changing the position of the light detection region by changing the optical path of the optical system of the microscope, the moving of the light detection region is quick, and since neither mechanical vibration nor hydrodynamic action occurs substantially in the sample solution, it is advantageous in that a measurement can be conducted under a stable condition without a single particle to be an object to be detected being influenced by dynamic actions.

In one of manners of the above-mentioned present invention, the number of single particles encompassed in the light detection region may be counted by counting the number of the signals (The counting of particles). In that case, by associating the number of the detected single particles with the moving amount of the position of the light detection region, the information on the number density or concentration of the single particle identified in the sample solution will be acquired. Concretely, for instance, the ratio of number densities or concentrations of two or more sample solutions or a relative ratio of a number density or concentration to a standard sample solution to be the reference of a concentration or a number density may be computed, or an absolute number density value or concentration value may be determined using a relative ratio of a number density or concentration to a standard sample solution to be the reference of a concentration or a number density. Or, by determining the whole volume of the moving track of the position of the light detection region by an arbitrary method, for example, by moving the position of the light detection region at a predetermined speed, the number density or concentration of the single particle can be concretely computed.

The processes of the optical analysis technique of conducting a light detection with moving the position of a light detection region in a sample solution and detecting the signal from each single particle individually in the above-mentioned inventive device, in which the presence or absence of a single particle is determined with reference to the probabilities of the occurrence of a pattern of a time variation of the detected light intensity value (the first and second occurrence probabilities), can be realized with a general-purpose computer.

Thus, according to another aspect of the present invention, there is provided a computer readable storage device having a computer program product including programmed instructions for optical analysis of detecting light from a light-emitting particle dispersed and moving at random in a sample solution using an optical system of a confocal microscope or a multiphoton microscope, said programmed instructions causing a computer to perform steps comprising: moving a position of a light detection region of the optical system of the microscope in the sample solution; measuring a light intensity from the light detection region during the moving of the position of the light detection region in the sample solution to generate light intensity data; computing a first occurrence probability in assuming a first condition that no single particles exist in the light detection region and a second occurrence probability in assuming a second condition that a single particle exists in the light detection region for a time variation of light intensity value in each analysis window set out in time series on the time series light intensity data; and detecting a signal indicating an existence of each single particle on the time series light intensity data based on the first and second occurrence probabilities. In this case, as in the inventive device, typically, in the procedure of detecting the light from the light detection region to generate time series light intensity data, the light from the light detection region is detected by the photon counting in which (a) photon(s) arriving in every predetermined measuring unit time (bin time) is/are counted, and in that case, the time series light intensity data becomes time series photon count data. The "analysis window" may be set in the same manner as in the inventive device. When a particles to be an observation object is a light-emitting particle, "a temporary increase of light intensity value" on the time series light intensity data is "a signal indicating an existence of each of single particles". And, when a particle to be an observation object is a non-light-emitting particle (in a detected wavelength band), the light from the light detection region includes a significant background light, and a temporary reduction of the light intensity from the background light is "a signal indicating an existence of each of single particles". In this regard, the computer program is provided while being memorized in a computer readable storage medium. A computer reads out the program memorized in the storage device and realizes the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

Also in the above-mentioned structure, typically, the first and second occurrence probabilities may be computed based upon the light intensity value in each unit time and the expected value in each unit time in assuming the first and second conditions in an analysis window, respectively, and more concretely, under an assumption that the light intensity value in each unit time follows the Poisson distribution having an expected value in each unit time, a unit time occurrence probability of the light intensity value in each unit time may be computed, and the first and second occurrence probabilities each may be computed using the corresponding unit time occurrence probabilities. And, it may be judged that a single particle has existed in the light detection region in the time of an analysis window in which the second occurrence probability is larger than the first occurrence probability, or alternatively, a time region in which a single particle has existed in the light detection region may be determined based on an odds ratio of the second occurrence probability and the first occurrence probability.

Further, the computer program in the above-mentioned computer readable storage device may also be designed such that at least two mutually different components of the light from the light detection region are detected separately: time series light intensity data of each of the components is generated: the first occurrence probability and the second occurrence probability that is a function of a predetermined characteristic value of a single particle to be an observation object are further computed for each of the components; and a signal indicating an existence of a single particle possessing the predetermined characteristic value on the time series light intensity data is detected based on the first occurrence probability and the second occurrence probability for each of the components. And, in a case that the single particles include single particles of two or more kinds having mutually different predetermined characteristic values, in the above-mentioned computer program, for each of the kinds of single particle, the second occurrence probability of each of the components that is a function of the mutually different predetermined characteristic values may be computed and a signal indicating an existence of a single particle may be detected by the kind on time series light intensity data based on the first occurrence probability of each of the components and the second occurrence probability of each of the components for each of the two or more kinds of single particle.

Furthermore, the moving speed of the position of the light detection region in the sample solution may be appropriately changed based on the characteristics, the number density or concentration of the single particle in the sample solution, and preferably, the moving speed of the position of the light detection region in the sample solution is set higher than the diffusion moving velocity of the single particle to be the object to be detected. The moving of the position of the light detection region in the sample solution may be conducted by an arbitrary way, and preferably, the position of the light detection region may be changed by changing the optical path of the optical system of the microscope or by moving the position of the sample solution. The movement track of the position of the light detection region may be set arbitrarily, for example, selected from circular, elliptical, rectangular, straight linear, and curvilinear ones.

Also in the above-mentioned computer program, there may be comprised a step of counting the number of the single particles detected during the moving of the position of the light detection region by counting the number of the signals from the single particles detected individually and/or a step of determining the number density or concentration of the single particle in the sample solution based on the number of the detected light-emitting particles.

According to the above-mentioned inventive device or computer program, there is realized a novel optical analysis method of conducting the detection of light of each particle with moving the position of a light detection region in a sample solution, in which the presence or absence of a single particle is determined with reference to the probabilities of the occurrence of a pattern of a time variation of the detected light intensity value (the first and second occurrence probabilities)

Thus, according to the present invention, there is further provided a method of detecting a single particle dispersed and moving at random in a sample solution using an optical system of a confocal microscope or a multiphoton microscope, comprising steps of: moving a position of a light detection region of the optical system of the microscope in the sample solution, measuring a light intensity from the light detection region during the moving of the position of the light detection region in the sample solution to generate light intensity data; computing a first occurrence probability in assuming a first condition that no single particles exist in the light detection region and a second occurrence probability in assuming a second condition that a single particle exists in the light detection region for a time variation of light intensity value in each analysis window set out in time series on the time series light intensity data; and detecting a signal indicating an existence of each single particle on the time series light intensity data based on the first and second occurrence probabilities. In this case, as in the inventive device, typically, in the step of detecting the light from the light detection region to generate time series light intensity data, the light from the light detection region is detected by the photon counting in which (a) photon(s) arriving in every predetermined measuring unit time (bin time) is/are counted, and in that case, the time series light intensity data becomes time series photon count data. The "analysis window" may be set in the same manner as in the inventive device. When a particles to be an observation object is a light-emitting particle, "a temporary increase of light intensity value" on the time series light intensity data is "a signal indicating an existence of each of single particles". And, when a particle to be an observation object is a non-light-emitting particle (in a detected wavelength band), the light from the light detection region includes a significant background light, and a temporary reduction of the light intensity from the background light is "a signal indicating an existence of each of single particles".

Also in the above-mentioned structure, typically, the first and second occurrence probabilities may be computed based upon the light intensity value in each unit time and the expected value in each unit time in assuming the first and second conditions in an analysis window, respectively, and more concretely, under an assumption that the light intensity value in each unit time follows the Poisson distribution having an expected value in each unit time, a unit time occurrence probability of the light intensity value in every unit time may be computed, and the first and second occurrence probabilities each may be computed using the corresponding unit time occurrence probabilities. And, it may be judged that a single particle has existed in the light detection region in the time of an analysis window in which the second occurrence probability is larger than the first occurrence probability, or alternatively, a time region in which a single particle has existed in the light detection region may be determined based on an odds ratio of the second occurrence probability and the first occurrence probability.

Further, the above-mentioned method may also be designed such that at least two mutually different components of the light from the light detection region are detected separately; time series light intensity data of each of the components is generated; the first occurrence probability and the second occurrence probability that is a function of a predetermined characteristic value of a single particle to be an observation object are further computed for each of the components; and a signal indicating an existence of a single particle possessing the predetermined characteristic value on the time series light intensity data is detected based on the first occurrence probability and the second occurrence probability for each of the components. And, in a case that the single particles include single particles of two or more kinds having mutually different predetermined characteristic values, in the above-mentioned method, for each of the kinds of single particle, the second occurrence probability of each of the components that is a function of the mutually different predetermined characteristic values may be computed and a signal indicating an existence of a single particle may be detected by the kind on time series light intensity data based on the first occurrence probability of each of the components and the second occurrence probability of each of the components for each of the two or more kind of single particle.

Furthermore, the moving speed of the position of the light detection region in the sample solution may be appropriately changed based on the characteristics, the number density or concentration of the single particle in the sample solution, and preferably, the moving speed of the position of the light detection region in the sample solution is set higher than the diffusion moving velocity of the single particle to be the object to be detected. The moving of the position of the light detection region in the sample solution may be conducted by an arbitrary way, and preferably, the position of the light detection region may be changed by changing the optical path of the optical system of the microscope or by moving the position of the sample solution. The movement track of the position of the light detection region may be set arbitrarily, for example, selected from circular, elliptical, rectangular, straight linear, and curvilinear ones.

Also in the above-mentioned method, there may be comprised a step of counting the number of the single particles detected during the moving of the position of the light detection region by counting the number of the signals from the single particles detected individually and/or a step of determining the number density or concentration of the single particle in the sample solution based on the number of the detected light-emitting particles.

The optical analysis technique of the above-mentioned present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also.

Effect of Invention

Thus, according to the present invention, in the scanning molecule counting method, instead of simply referring to an increase or a decrease in the light intensity value on time series light intensity data, it is estimated whether a single particle exists in a light detection region or not by determining a condition in which the pattern of the time variation of light intensity value is prone to be generated. According to this structure, even in a case that the variation of the light intensity value owing to a single particle is comparatively small and thus it is difficult to discriminate between a particle signal and a noise signal only with the absolute value of the light intensity value variation, it is expected that more accurate discrimination between a particle signal and a noise signal becomes possible. Moreover, because of the improvement of the accuracy of discrimination between a particle signal and a noise signal, there is expected the expansion of the detectable concentration range of single particle in a sample solution to the lower concentration side in the scanning molecule counting method. Furthermore, in the use of the occurrence probability of a time variation of light intensity value, computed with consideration of a predetermined characteristic value of a single particle to be an observation object, the discrimination between the single particle to be an observation object and the other particles becomes possible, and accordingly, the improvement in the accuracy or sensitivity of the measurements is expected also in a sample solution containing impurities, etc.

Other purposes and advantages of the present inventions will become clear by explanations of the following preferable embodiments of the present invention.

BRIEF DESCRIPTIONS OF DRAWINGS

FIG. 1A is a schematic diagram of the internal structure of the optical analysis device with which the scanning molecule counting method according to the present invention is performed. FIG. 1B is a schematic diagram of a confocal volume (an observation region of a confocal microscope). FIG. 1C is a schematic diagram of the mechanism for changing the direction of the mirror 7 to move the position of a light detection region in a sample solution. FIG. 1D is a schematic diagram of the mechanism which moves the horizontal position of a micro plate to move the position of the light detection region in a sample solution.

FIGS. 2A and 2B are a schematic diagram explaining the principle of the detection of the light of a light-emitting particle and a schematic diagram of a time variation of the measured light intensity in the scanning molecule counting method to which the present invention is applied, respectively. FIGS. 2C and 2D are a schematic diagram explaining the principle of the detection of an existence of a single particle emitting no light and a schematic diagram of a time variation of the measured light intensity in the inverted scanning molecule counting method to which the present invention is applied, respectively.

FIG. 3A shows typical examples of time series light intensity data. (Left) A case that a light-emitting particle with large brightness exists. (Middle) A case that a light-emitting particle with small brightness exists. (Right) A case that no light-emitting particles exist. FIG. 3B is a drawing explaining the analysis window set on time series light intensity data in the present invention. FIG. 3C is a model drawing showing a manner of the motion of a light-emitting particle in a case that the particle passes through a light detection region by moving the position of the light detection region in a sample solution at a speed quicker than the diffusion moving speed of the light-emitting particle. FIG. 3D is a schematic diagram of the intensity distribution of light, emitted from a light-emitting particle in a light detection region and detected, in the direction of radius r of the light detection region FIG. 4A shows time series light intensity data schematically expressed for the purpose of explanation, in which the upper row shows expected values of light intensity value on the time series light intensity data in assuming the condition where a light-emitting particle exists (Left: the second condition) and the condition where no light-emitting particles exist (Right: the first condition), respectively; the middle row shows actually measured light intensity values; and the lower row shows the occurrence probabilities of the measured light intensity value in assuming the condition where a light-emitting particle exists (Left) and the condition where no light-emitting particles exist (Right), respectively. FIG. 4B shows a model figure (upper) of polarized light components of the light emitted from a light-emitting particle; an average time variation of the light intensity value of each component (lower left), and an average time variation of all the light intensity values (lower right). FIG. 4C shows emission wavelength spectrums of light-emitting particle D1 and D2 possessing mutually different emission wavelength characteristics, where, in a case of detecting components of the light of mutually different wavelength bands separately, the light intensity value of each component from a light-emitting particle detected in each wavelength band is shown. The area of a shaded portion is equivalent to the light intensity value of each component.

FIG. 5 shows in the form of a flow chart the procedures of the scanning molecule counting method performed according to the present invention.

FIGS. 6A, 6B and 6C show a part of time series light intensity data (photon count data) (FIG. 6A) obtained by the scanning molecule counting method in accordance with the present invention: smoothed time series light intensity data (FIG. 6B) obtained by carrying out the smoothing of the time series light intensity data of (FIG. 6A); and odds ratio (FIG. 6C) of occurrence probabilities (the second and first occurrence probabilities) of the time series light intensity data of (FIG. 6A), computed with assuming a case that a particle exists and a case that no particles exist, respectively, according to the teaching of the present invention.

Figure 9A:
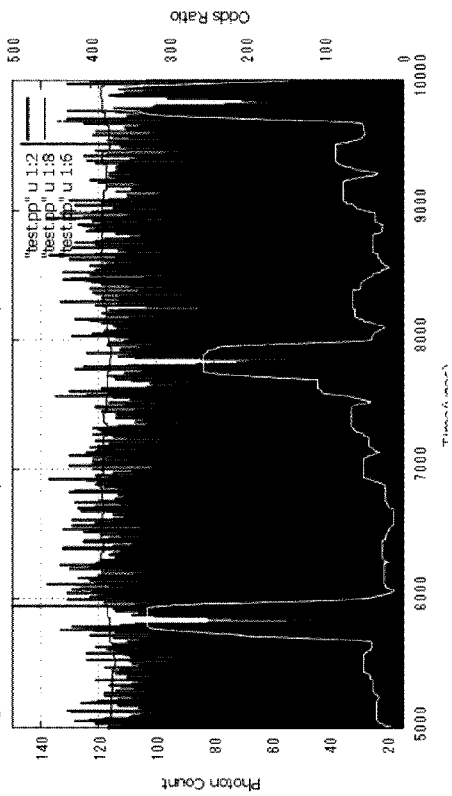
Figure 9B:
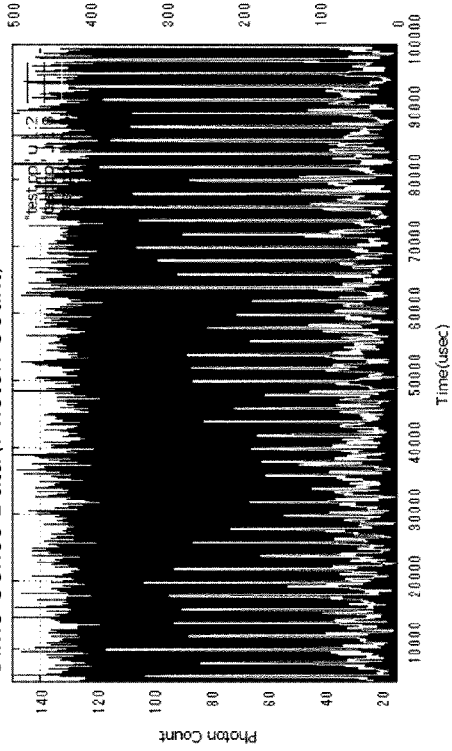

FIG. 9A shows a part of time series light intensity data (photon count data) (upper row) obtained by the inverted scanning molecule counting method in accordance with the present invention; and odds ratio (lower row) of occurrence probabilities (the second and first occurrence probabilities) of that time series light intensity data, computed with assuming a case that a particle exists and a case that no particles exist, respectively, according to the teaching of the present invention. FIG. 9B is enlarged diagrams of the part of FIG. 9A.

FIG. 10 are further enlarged diagrams of FIG. 9B.

FIG. 11A is a diagram showing the relation between particle concentrations in a sample solution and the number of detected particles in a case that detection and counting of particles were performed by the inverted scanning molecule counting method in accordance with the present invention; and FIG. 11B is a diagram showing the relation between particle concentrations in sample solutions and the number of particles detected through the smoothing and the fitting of a bell shaped function in the same time series light intensity data as in FIG. 11A. In the diagram, the error bar is the standard deviation.

FIG. 12 shows results of detection of light-emitting particles and identification of kinds of light-emitting particle in the time series light intensity data obtained by detecting separately components of mutually different polarization directions in light measurement, using the occurrence probabilities computed with consideration of the polarization fluorescence anisotropy of a light-emitting particle, by the scanning molecule counting method in accordance with the present invention. In the diagram, the left shows discrimination results of the kinds of light-emitting particle detected in a solution containing plasmid and the right shows discrimination results of kinds of light-emitting particle detected in a solution containing fluorescent dye (TAMRA).

EXPLANATIONS OF REFERENCE NUMERALS

1 - - - Optical analysis device (confocal microscope)
2 - - - Light source
3 - - - Single mode optical fiber
4 - - - Collimating lens
5 - - - Dichroic mirror
6, 7, 11 - - - Reflective mirror
8 - - - Objective
9 - - - Micro plate
10 - - - Well (sample solution container)
12 - - - Condenser lens
13 - - - Pinhole
14 - - - Barrier filter
14a - - - Dichroic mirror or beam splitter
15 - - - Multi-mode optical fiber
16 - - - Photodetector
17 - - - Mirror deflector
17a - - - Stage position changing apparatus
18 - - - Computer

DESCRIPTION OF EMBODIMENTS

In the followings, preferable embodiments of the present invention are described in detail.

Structure of Optical Analysis Device

Figure 1A:
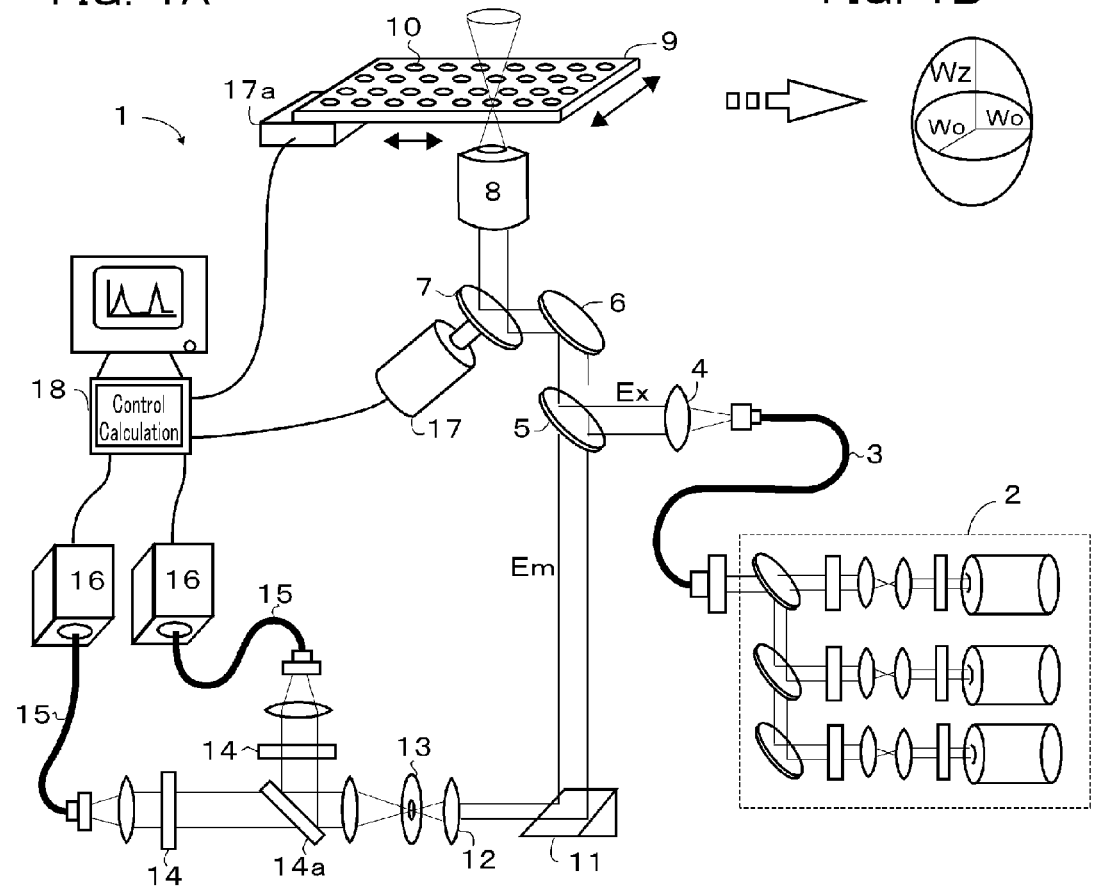

In the basic structure, an optical analysis device which realizes the optical analysis technique according to the present invention is a device constructed by associating the optical system of a confocal microscope and a photodetector, enabling FCS, FIDA, etc., as schematically illustrated in FIG. 1A. Referring to this drawing, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light, emitted from a light source 2 and transmitted through the inside of a single mode fiber 3 (Ex), forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of µL of a sample solution is dispensed, and the laser light emitted from the objective 8 is focused in the sample solution in the sample container or well 10, forming a region having strong light intensity (excitation region).

In a case that a single particle to be an observation object is a light-emitting particle, light-emitting particles, which are typically fluorescent particles or particles to which a light emitting label such as a fluorescent dye is attached, are dispersed or dissolved in the sample solution, and when such a light-emitting particle enters into the excitation region, the light-emitting particle is excited and emits light during dwelling in the excitation region. On the other hand, in a case that a single particle to be an observation object is a non-light-emitting particle, typically, particles which emit no light in the detected wavelength band and an arbitrary light-emitting substance producing background light are dispersed or dissolved in the sample solution, and when no particles emitting no light in the detected wavelength band are present in the excitation region, substantially constant light is emitted by the light-emitting substance being excited, so that the light becomes the background light: and when a particle emitting no light in the detected wavelength band enters into the excitation region, the background light will be reduced.

Figure 1B:
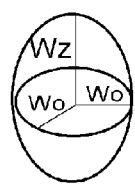

Then, the light (Em), emitted from the excitation region and passing through the objective 8 and the dichroic mirror 5, is reflected on the mirror 11 and condensed by a condenser lens 12, and then the light passes through the pinhole 13; transmits through the barrier filter 14 (where a light component only in a particular wavelength band is selected); and is introduced into a multimode fiber 15, reaching to the corresponding photodetector 16, and after the conversion into time series electric signals, the signals are inputted into the computer 18, where the processes for optical analyses are executed in manners explained later. In this regard, as known in ones skilled in the art, in the above-mentioned structure, the pinhole 13 is located at a conjugate position of the focal position of the objective 8, and thereby only the light emitted from the focal region of the laser light. i.e., the light detection region, as schematically shown in FIG. 1B, passes through the pinhole 13 while the light from regions other than the light detection region is blocked. The focal region of the laser light illustrated in FIG. 1B is a light detection region, whose effective volume is usually about 1-10 fL in this optical analysis device (typically, the light intensity is spread in accordance with a Gaussian type distribution having the peak at the center of the region. The effective volume is a volume of an approximate ellipsoid bordering a surface where the light intensity is reduced to $1/e^2$ of the center light intensity.), which focal region is called as "confocal volume". Furthermore, in the present invention, since the light from a single light-emitting particle, for example, the faint light from one fluorescent dye molecule, or the reduction of the background light by the existence of a non-light-emitting particle, is detected, preferably, a super high sensitive photodetector, usable for the photon counting, is used for the photodetector 16. When the detection of light is performed by the photon counting, the measurement of light intensity is performed for a predetermined time in a manner of measuring the number of photons which have sequentially arrived at a photodetector in every measuring unit time (BIN TIME). Thus, in this case, the time series light intensity data is time series photon count data. Also, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18. According to this structure, quick measurement can be achieved even when there are two or more specimens.

Figure 1C:
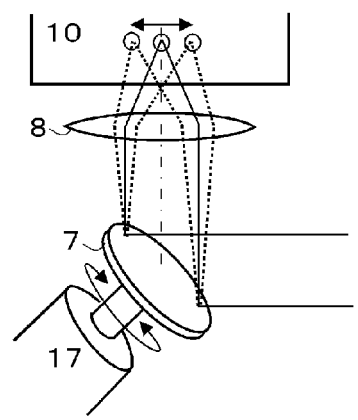
Figure 1D:
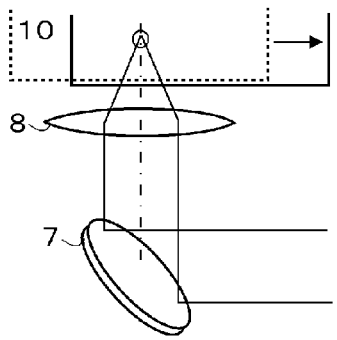

Furthermore, in the optical system of the above-mentioned optical analysis device, there is further provided a mechanism to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C (the type of moving the absolute position of a light detection region). This mirror deflector 17 may be the same as that of a galvanomirror device equipped on a usual laser scan type microscope. Or, alternatively, as illustrated in FIG. 1D, the stage position changing apparatus 17a may be operated in order to move the horizontal position of the container 10 (micro plate 9), into which the sample solution has been dispensed, to move the relative position of the light detection region in the sample solution (the type of moving the absolute position of a sample solution). In either of the ways, in order to attain a desired moving pattern of the position of the light detection region, the mirror deflector 17 or the stage position changing apparatus 17a is driven in harmony with the light detection of the photodetector 16 under the control of the computer 18. The movement track of the position of the light detection region may be arbitrarily selected from circular, elliptical, rectangular, straight and curvilinear ones, or a combination of these (The program in the computer 18 may be designed so that various moving patterns can be selected.) In this regard, although not illustrated, the position of the light detection region may be moved in the vertical direction by moving the objective 8 or stage up and down.

In the case that the light-emitting particle to be an object to be observed or the substance providing the background light emits light by multiple photon absorption, the above-mentioned optical system is used as a multiphoton microscope. In that case, since the light is emitted only from the focal region of the excitation light (light detection region), the pinhole 13 may be removed. Further, in the case that the light-emitting particle or the substance providing the background light emits light owing to a chemiluminescence or bioluminescence phenomenon without excitation light, the optical system 2-5 for generating excitation light may be omitted. When a light-emitting particle or substance providing the background light emits light owing to phosphorescence or scattered light, the above-mentioned optical system of the confocal microscope is used as it is. Furthermore, in the optical analysis device 1, as shown in the drawing, two or more excitation light sources 2 may be provided so that the wavelength of the excitation light can be appropriately selected in accordance with the wavelength of the light for exciting a light-emitting particle or substance providing the background light.

Moreover, there may also be equipped with two or more photodetectors 16, such that each of the photodetectors 16 may be designed to detect separately one of mutually different components of the light from the light detection region. As described in detail later, it becomes possible to detect selectively a single particle possessing a particular light-emitting characteristic by appropriately choosing the components to be detected. In a case of detecting such mutually different components of light from the light detection region, there is provided a mechanism for dividing an optical path in an arbitrary manner in the detected light optical path after the pinhole 13, For example, in a case of dividing the light from the light detection region into mutually different polarized light components, a polarization beam splitter 14a is inserted into a site, designated 14a, of the detected light optical path. In this case, a polarizer (not shown) is inserted into the excitation light optical path. In addition, by inserting to the site 14a of the detected light optical path a dichroic mirror 14a which reflects light of a particular wavelength band and allows the transmission of another wavelength band, the light components of mutually different wavelength bands become separately detectable.

The computer 18 has performs a CPU and a memory, and the inventive procedures are performed through the CPU executing various operational processings. In this regard, each procedure may be done with hardware. All or a part of processes explained in this embodiment may be performed by the computer 18 with a computer readable storage device having memorized the programs to realize those processes. Accordingly, the computer 18 may read out the program memorized in the storage device and realize the above-mentioned steps by performing the processing and calculations of information. Here, a computer readable storage device may be a magnetic disk, a magnetic optical disk, a CD-ROM, a DVD-ROM, a semiconductor memory, etc. Furthermore, the above-mentioned program may be distributed to a computer through communication line, and the computer which has received this distribution may be made to execute the program.

The Principle of the Inventive Optical Analysis Technique

As described in the column of "Summary of Invention", in the inventive optical analysis technique, briefly, for detecting a signal of a single particle to be an observation object from time series light intensity data measured and obtained with moving the position of a light detection region in the scanning molecule counting method or the inverted scanning molecule counting method, instead of simply referring to an increase or a decrease of light intensity value on the time series light intensity data, it is estimated in which of a case that a particle exists in the light detection region and a case that no particle exist in the light detection region a pattern of a time variation of the measured light intensity value is a pattern which is generated at the higher probability. Then, based on the estimated results, there are detected the presence or absence of the existence of a signal of a single particle to be an observation object and their number on the time series light intensity data. Hereafter, the principle of the scanning molecule counting method and the detection of a signal of a single particle to be an observation object in the present invention will be explained about.

1. Principle of Scanning Molecule Counting Method

Figure 2A:
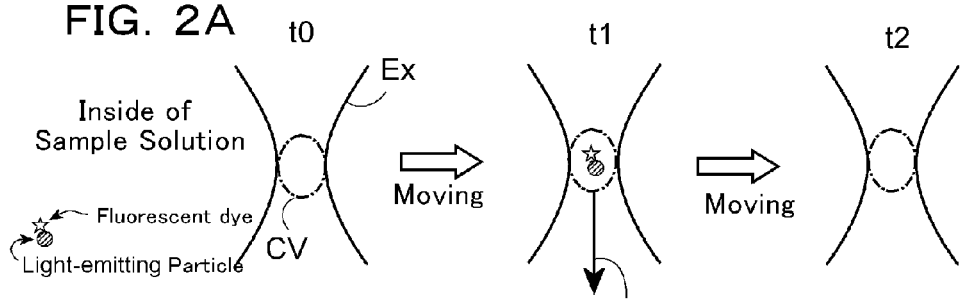
Figure 2B:
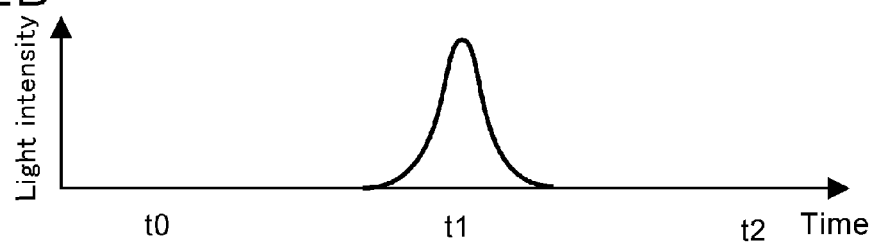

In the basic processes performed in the scanning molecule counting method, as described in patent documents 9-11, briefly speaking, the light detection is performed together with moving the position of the light detection region CV in a sample solution, namely, scanning the inside of the sample solution with the light detection region CV by driving the mechanism (mirror deflector 17) for moving the position of the light detection region to change the optical path or by moving the horizontal position of the container 10 (micro plate 9) into which the sample solution is dispensed, as schematically drawn in FIG. 2A. Then, in a case that a particle to be observed is a light-emitting particle, during the moving of the light detection region CV (in the drawing, time t0-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Then, by detecting, one by one, each pulse form signal (significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired.

Figure 2C:
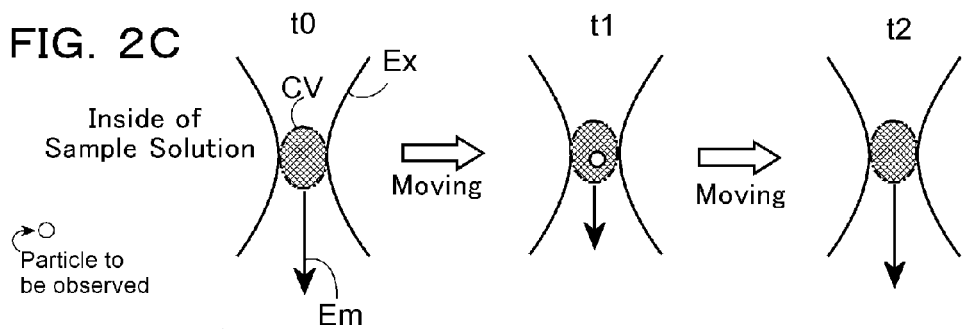
Figure 2D:
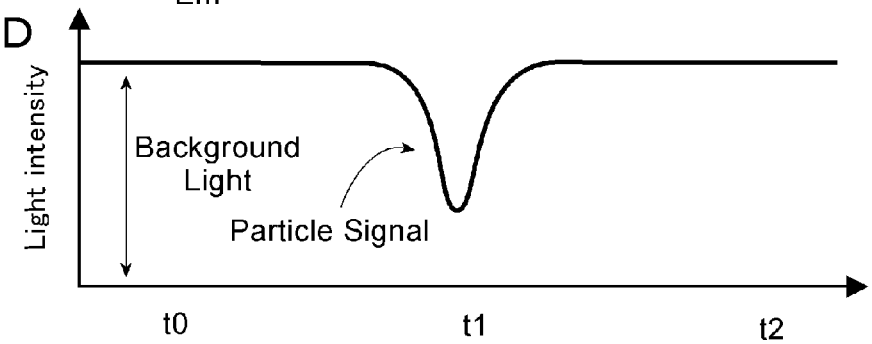

Further, in a case that a particle to be an observation object is a non-light-emitting particle, in the light measurement by the above-mentioned scanning molecule counting method, it becomes possible to detect the existence of a non-light-emitting particle by making background light emit from a light detection region (or illuminating a light detection region in a illumination light) and capturing a reduction of the background light which is detected when a particle to be an observation object enters into the light detection region (the inverted scanning molecule counting method). In this case, more concretely, as schematically drawn in FIG. 2C, the light detection is performed together with moving the position of the light detection region CV in a sample solution. Here, when light-emitting substance has been dispersed in the sample solution, much light-emitting substance exist in the light detection region CV so that the light from those light-emitting substance will be detected almost uniformly during the moving of the light detection region CV (in the drawing, time t0-t2). However, when the light detection region CV, during its moving, passes through a region where a single, non-light-emitting particle exists (t1), the volume of the occupied region of the light-emitting substance decreases, and thereby the total amount of the light emitted by the light-emitting substance decreases, and therefore, as drawn in FIG. 2D), a significant reduction of light intensity (Em) in a bell-shaped pulse form will appear on time series light intensity data. Thus, by performing the above-mentioned moving of the position of the light detection region CV and the light detection, and detecting, one by one, a significant light intensity reduction appearing in pulse form as illustrated in FIG. 2D during the moving of the position of the light detection region CV and the light detection, namely, a signal indicating an existence of a non-light-emitting particle, non-light-emitting particles are detected individually, and by counting their number, the information about the number, concentration or the number density of the single particles existing in the measured region can be acquired.

By the way, in the scanning molecule counting method as described above, there exist increases of light intensity value due to heat noise, stray light the Raman scattering of water, etc. (noise signal) on actually measured time series light intensity data, other than the signals of light-emitting particles. Further, in the case of the inverted scanning molecule counting method, there exist reductions of light intensity value due to the fluctuation of the intensity of the background light (hereafter, also in this case, referred to as noise signals.). Then, in performing detecting a signal of a single particle on time series light intensity data, first, a pulse form signal is detected, and then, the intensity time width and shape of the detected pulse form signal are tested: only a signal which conforms to the conditions of the intensity, time width, and shape of a signal which should be acquired when a single particle passes through the light detection region is judged as a signal of a single particle, and the other signals are judged as noise signals.

Figure 3A:
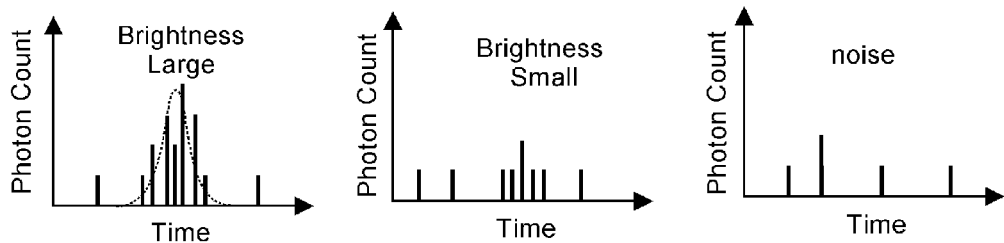

However, when the intensity value of a signal of a single particle becomes weak, the discrimination between a signal of a single particle and a noise signal based on the intensity, time width and shape of a signal becomes difficult. Especially in the case that a particle to be observed is a light-emitting particle, the number of photons emitted from a light-emitting particle is minute and photons are emitted stochastically, and thus, actually, the profile of light intensity value does not form a smooth bell shape as drawn on FIG. 2B but it becomes discrete as illustrated in FIG. 3A left. Accordingly, in a case that the number of photons emitted from a light-emitting particle decreases, the intensity, time width and shape of a signal on the light intensity data in that case (FIG. 3A middle) would be difficult to be discriminated from those of the light intensity data in a case that no particles exist but only a noise signal exists (FIG. 3A right). Also, the intensity value of light which is emitted from a light-emitting particle in a light detection region and detected decreases as the position of the light-emitting particle becomes more apart from the almost center of the light detection region (refer to FIG. 3D), and the number of light-emitting particles increases as it is more away from the almost center of the light detection region, and therefore, the number of signals of particles which would be difficult to discriminate from noise signals increases. Such situations occur also in the case of a reduction of the number of photons of the background light in the inverted scanning molecule counting method in which a particle to be observed is a non-light-emitting particle.

In the scanning molecule counting method and the inverted scanning molecule counting method, the accuracy and/or sensitivity are improved as the detection precision and the detected number of particle signals per a certain moving length of a light detection region become higher. However, as noted above, when the reference value of the intensity of a signal for the judgment is reduced for increasing the detected number of the particle signals, the possibility of judging a noise signal erroneously as a particle signal increases, and if the reference value of the intensity of a signal for the judgment is increased for improving the detection precision of a particle signal, many particle signal having low brightness could not be detected. Then, in the present invention, there is proposed a novel algorithm enabling more accurately the detection of a signal of a single particle which is difficult to discriminate from noise signals in accordance with the intensity, time width and shape of the signal.

2. Detection of a Signal of a Single Particle

In a case where time series light intensity data is photon count data, the light intensity value is a detected photon count per bin time. Thus, as schematically illustrated in FIG. 3A, the light intensity value is discretely distributed in the time base direction. In that case, a particle signal with large brightness is less influenced with noise signals and has an approximately bell shaped profile (Left figure): however, as for a particle signal with small brightness, its intensity value becomes almost similar to that of a noise signal and a noise signal is further superposed thereon (Middle figure), and thus, it becomes difficult to extract the approximately bell shaped profile, and so, its discrimination from a time region in which only a noise signal exists without particles (right figure) becomes difficult. However, between the time region in which a particle signal with small brightness exists and the time region in which only noise signals exist, there are differences in the occurrence frequency and the patterns of phenomena of a photon being detected (phenomena that the photon count becomes one or more). That is, as understood also from the drawings, in the case of a noise signal, the phenomenon of the photon detection always occurs at random; but, in the case of a particle signal, the phenomenon of the photon detection concentrates in time, and especially, there is a tendency that the intensity values around its center become higher. The same phenomenon is observed also between a signal of a non-light-emitting particle and the fluctuation of the background light.

Thus, in the present invention, noticing the differences in the occurrence frequency and pattern of the phenomena of the photon detection, it is tried to detect a particle signal selectively. To do this, in the novel algorithm for detection of a single particle signal according to the present invention, with respect to the time variation of light intensity value (photon count sequence) in each predetermined time width on time series light intensity data, there are computed a probability that said time variation of light intensity value would occur in assuming that a particle exists in the light detection region (the occurrence probability (in the presence of a particle), the second occurrence probability), and a probability that said time variation of light intensity value would occur in assuming that no particles exists in the light detection region (the occurrence probability (in the absence of particles), the first occurrence probability). Then, it is estimated that the condition which gives the higher occurrence probability is the actual condition.

Figure 3B:
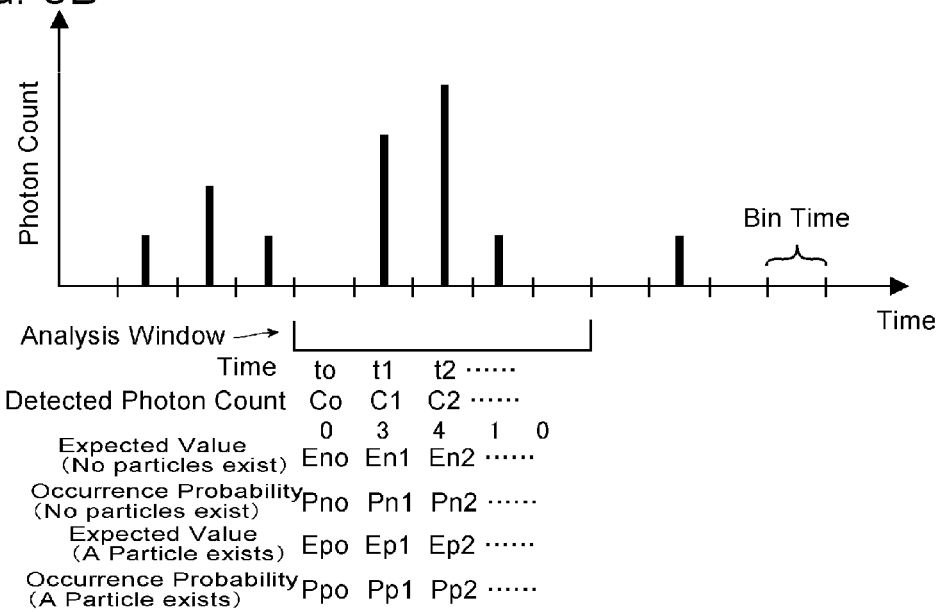

More concretely, first, referring to FIG. 3B, in time series light intensity data, there are set sections of an arbitrary time width (hereafter, called as an analysis window). The analysis window has a photon count Ci detected in each unit time (usually, it may be a bin time.), ti, (i=1, 2, - - - the same in the following.). By the way, it is thought that the number of events of photon detections occurring in each unit time follows the Poisson distribution having the expected value in the corresponding unit time, and therefore, in an arbitrary unit time ti, a probability that the detected photon count Ci occurs (unit time occurrence probability) is given by:

[Exp. 1]
$$Pi = \frac{Ei^{Ci}}{Ci!}\exp(-Ei) \quad (1)$$

Here, Ei is the expected value of the photon count in the unit time ti. And when n+1 unit times are included in an analysis window, the probability P that the detected photon count sequence Ci occurs in the analysis window (occurrence probability) is given by:

[Exp. 2]
$$P = \prod_{i=0}^{n} Pi \quad (2)$$

The above-mentioned expected value Ei of the number of the occurrences of the photon detection events in each unit time ti is determined depending upon the presence or absence of a particle in the light detection region in a time region corresponding to an analysis window under the light measurement. Thus, when no particle exist in the light detection region, since the photon detection event always occurs at random, the expected value Eni in each measuring unit time ti may be set to:

$$Eni = Bg \quad (3)$$

Here, Bg is the time average value of noise signals in a case that a particle to be observed is a light-emitting particle, and the time average value of the background light in a case that a particle to be observed is a non-light-emitting particle. Thus, by substituting the value of Expression (3) into Expression (1), the unit time occurrence probability Pni in each measuring unit time ti is computed in time series, and, further, the probability Pn (the first occurrence probability) that the actual detected photon count sequence would occur when the condition that no particle exist in the light detection region is assumed is computed with Expression (2).

Figure 3C:
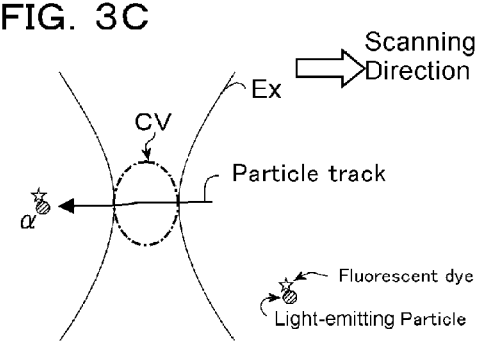
Figure 3D:
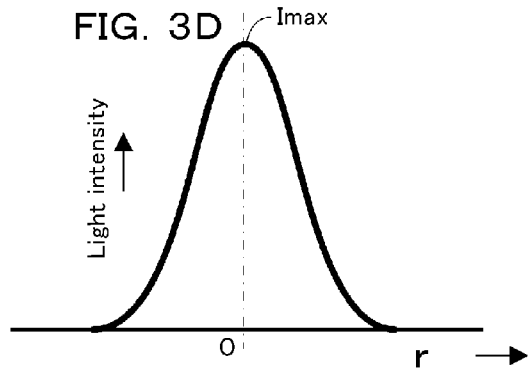

On the other hand, in a case that a particle exists in the light detection region, since the position of the light detection region CV is moving, a particle will pass through the inside of the light detection region CV as schematically drawn in FIG. 3C. In this process, the intensity value of light emitted from the particle in the light detection region and detected or the reduction amount of the background light reduced when the particle exists in the inside of the light detection region is decreased as the position of the particle becomes more apart from the almost center of the light detection region as shown in FIG. 3D. Thus, the expected value Epi in each unit time ti when a particle exists in the light detection region is also shown as a bell shaped function in which the time is a variable. Here, supposing the bell shaped function is approximated by a Gauss function, the expected value Epi is given by:

[Exp. 3]

$$Epi = Q \cdot \exp\left(-\frac{(ti-tc)^2}{2W^2}\right) + Bg \quad (4)$$

Here, it is assumed that the Gauss function has the peak intensity Q in arbitrary time tc in an analysis window (for example, the center of the analysis window). Moreover, the full width at half maximum of the Gauss function of Expression (4) is equal to the time d/v for the light detection region with the moving speed v to pass through the full width at half maximum, d, of a distribution in the radius r direction of the light intensity value emitted from a particle in the light detection region and detected or the reduction amount of the background light reduced due to the existence of a particle in the inside of the light detection region as illustrated in FIG. 3D, and accordingly, from this condition, w is given by:

[Exp. 4]

$$w = \frac{1}{2\sqrt{2\ln 2}} \frac{d}{v} \quad (5)$$

In this regard, the full width at half maximum d of FIG. 3D can be determined from the optical system.

In the case that a particle to be observed is a light-emitting particle, supposing the total of the photon counts in an analysis window is consistent to the total of the expected value of Expression (4), the peak intensity Q in Expression (4) is given by:

[Exp. 5]

$$Q = \frac{\sum_{k=0}^{a}(Ci - Bg)}{w\sqrt{2\pi}} \quad (6)$$

On the other hand, in the case that a particle to be observed is a non-light-emitting particle, by setting that the expected value of the absolute value of the reduction amount of the photon count follows Expression (4), the peak intensity Q is given by:

[Exp. 6]

$$Q = \frac{\sum_{i=0}^{n}(Bg - Ci)}{w\sqrt{2\pi}} \quad (7)$$

Then, by substituting the value of Expression (4) to Expression (1), the unit time occurrence probability Ppi in each measuring unit time ti is computed in time series, and further, the probability Pp that the actual detected photon count sequence would occur when the condition that a particle exists in the inside of the light detection region is assumed (the second occurrence probability) is computed with Expression (2). Thus, when the occurrence probability Pp of the detected photon count sequence in assuming the condition that a particle exists exceeds with a certain degree beyond the occurrence probability Pn of the detected photon count sequence in assuming the condition that no particles exist, it is judged that the signal of a particle exits in this analysis window.

Figure 4A:
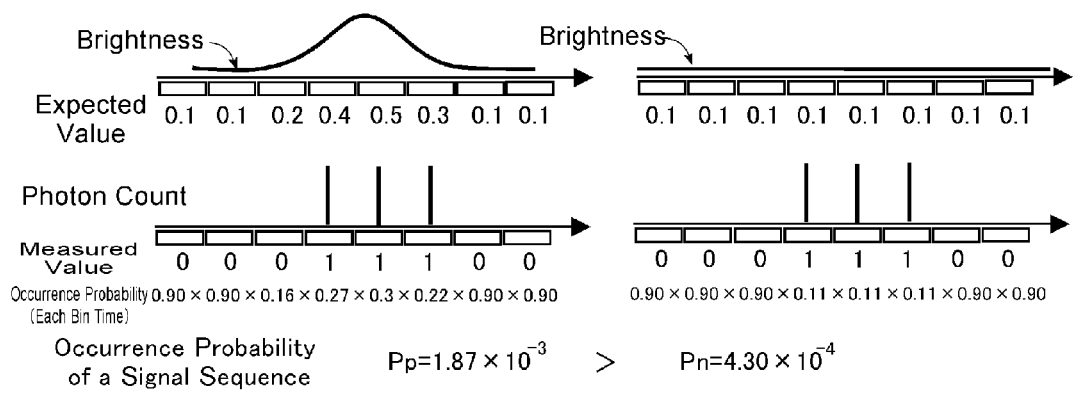

FIG. 4A shows an example of a series of the above-mentioned processes. Referring to the drawing, in the example of the drawing, when the photon count sequence whose photon counts are [00011100] in this order in the respective unit times (rectangle) on the time base (the arrow) is detected as in the middle row of the drawing, supposing the average of the background light is 0.1 as in the upper row right drawing, the expected value of each unit time in assuming that no particle exist becomes 0.1 over the whole region. On the other hand, the expected values of the respective unit times in assuming that a particle exists become the values having a bell shaped profile as in the upper row left drawing in accordance with Expression (6) using the detected photon counts and further Expression (4) using the result of Expression (6). Then, with Expression (1) using the detected photon count in each unit time and the expected value, the probability that the detected photon count would occur for each unit time (the occurrence probability for each bin time) is computed in each of the case that it is assumed that no particles exist (Lower row right) and the case that it is assumed that a particle exists (Lower row left). And, for the detected photon count sequence, the occurrence probability Pn of the photon count sequence in assuming that no particles exist and the occurrence probability Pp of the photon count sequence in assuming that a particle exists are computed by multiplying all those probabilities that those detected photon counts will occur in accordance with Expression (2), respectively. In the illustrated example, since the occurrence probability Pp>the occurrence probability Pn is established, the detected photon count sequence is judged as a signal of a particle.

In this connection, in an embodiment, for the judgment of whether a signal of a particle exists in an analysis window or not, the odds ratio OR of the occurrence probability Pp and the occurrence probability Pn:

$$OR = Pp(1-Pn)/(1-Pp)Pn \quad (8)$$

may be computed, and when its magnitude exceeds beyond a predetermined value, the existence of a signal of a particle in an analysis window may be judged.

In the above-mentioned detection processes of a signal of a particle, preferably, the analysis window is set to have more than the time width taken for a single particle to pass through the inside of the light detection region. Supposing a light detection region of radius r is moving at a velocity v, the time width of an analysis window will be set to be longer than:

$$2r/v \tag{9}$$

Further, preferably, an analysis window may be set successively for every unit time on time series light intensity data. According to this setting, the occurrence probability Pp, the occurrence probability Pn and/or the odds ratio OR will be computed along with the time series light intensity data. However, in that case, since the operation amounts will increase, an analysis window may be set for every several unit times. Furthermore, the analysis window may be set by dividing time series light-intensity data by the time width of the analysis window. In this case, the analysis windows will be set without overlapping mutually.

In the case that an analysis window is set for every unit time, when one particle signal exists, the judgment of the existence of the signal of the particle continues in the successive analysis windows. Namely, the signal of one particle corresponds to one section in which the judgment of the existence of the signal of the particle continues. Accordingly, the counting of signals of particles can be attained by counting the number of the sections in which the judgment of the existence of the signal of the particle continues. Further, in the above-mentioned detection processes of a signal of a particle, the bin time is set to a time not more than the time taken for a single particle to pass through the inside of the light detection region (Expression 9). This is for capturing the signal during the passing of a single particle over two or more bin times to detect the pattern of a time variation of light intensity value during the passing of the single particle (If the bin time is longer than the time of Expression 9, the pattern of the time variation of the light intensity value during the passing of the single particle could not be caught.).

3. Detection of Single Particle Signal Using Measurement of Two or More Light Components The above-mentioned method of detecting a single particle signal using the occurrence probabilities Pp and Pn can be extended to a case of measuring several mutually different light components separately to generate time series light intensity data for the respective components. In that case, by choosing components to be detected so that a light-emitting characteristic of a single particle to be an observation object can be reflected in the time series light intensity data for the respective components, it becomes possible to detect selectively a signal in which the light-emitting characteristic of a single particle to be the observation object is reflected. In the followings, several examples of detecting selectively a signal in which the light-emitting characteristic of a single particle is reflected will be explained about.

Figure 4B:
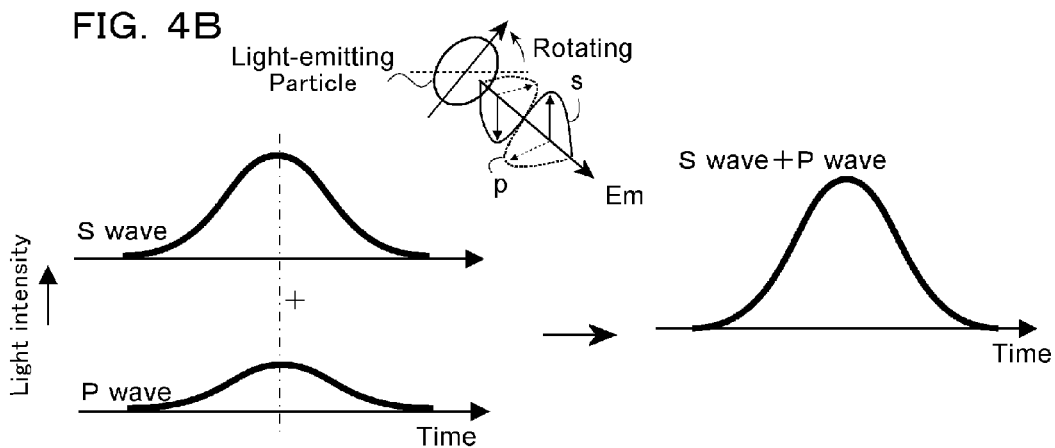

(i) Detection of a Signal of a Particle Possessing a Particular Polarization Characteristic In a case that light polarized in a fixed direction is employed as the excitation light and p wave and s wave fluorescence of a light-emitting particle are separately detected as detected lights, it becomes possible to detect selectively a signal of a particle possessing a particular polarization characteristic (Refer to FIG. 4B upper). First, using the light intensities Cp and Cs of the p wave and s wave of fluorescence, the fluorescence anisotropy R of a certain light-emitting particle is given as follows:

$$R=(Cp-Cs)/(Cp+Cs) \tag{10}$$

Thus, the ratio of the light intensities of the p wave and s wave of the fluorescence to the total fluorescence intensity (Cp+Cs) are given by:

$$Cp/(Cp+Cs)=\tfrac{1}{2}+R/2 \tag{11a}$$

$$Cs/(Cp+Cs)+\tfrac{1}{2}-R/2 \tag{11b},$$

respectively. By the way, as schematically drawn in FIG. 4B lower row, with respect to the sum of the light intensities of s wave and p wave of fluorescence, since the expected value Epi of the light intensity of each unit time in a certain analysis window when a particle exists is the same as that of Expression (4), the peak intensity Q is given by:

[Exp. 7]

$$Q = \frac{\sum_{i=0}^{n}(Cpi+Csi-Bgp-Bgs)}{2\sqrt{2\pi}} \tag{12}$$

Here, Cpi, Csi, Bgp and Bgs are the photon counts of the p wave and s wave and the intensities of the background light of p wave and s wave in each unit time, respectively. Further, the respective expected values Eppi and Epsi of the p wave and s wave of fluorescence in each unit time are given by:

$$Eppi=(\tfrac{1}{2}+R/2)Epi+Bgp \tag{13a}$$

$$Epsi=(\tfrac{1}{2}-R/2)Epi+Bgs \tag{13b}$$

Here, Epi is the value obtained by giving Q by Expression (12), and giving Bg by Bgp+Bgs in Expression (4). Thus, similarly to Expression (1), the occurrence probabilities Pppi and Ppsi of the detected photon counts in each unit time in the p wave and s wave of fluorescence in assuming that a particle exists are given by:

[Exp. 8]

$$Pppi = \frac{Eppi^{Cpi}}{Cpi!}\exp(-Eppi),$$

$$Ppsi = \frac{Epsi^{Csi}}{Csi!}\exp(-Epsi) \tag{14}$$

Accordingly, the occurrence probability Pp of the detected photon count sequence in an analysis window in assuming that a light-emitting particle which has a fluorescence anisotropy R exists is the product of all the occurrence probabilities Pppi and Ppsi, so that it can be given by:

[Exp. 9]

$$Pp = \prod_{i=0}^{n} Pppi \times \prod_{i=0}^{n} Ppsi = \prod_{i=0}^{n}(Pppi, Ppsi) \tag{15}$$

On the other hand, when it is assumed that no particle exist, the occurrence probability Pn of the detected photon count sequence in an analysis window becomes:

[Exp. 10]

$$Pn = \prod_{i=0}^{n} Pnpi \times \prod_{i=0}^{n} Pnsi = \prod_{i=0}^{n} (Pnpi, Pnsi) \quad (16)$$

Here, Pnpi and Pnsi are the occurrence probabilities in each unit time in the respective components, and thus, similarly to Expression (1), using the background lights Bgp, Bgs as the expected values, those become:

[Exp. 11]

$$Pnpi = \frac{Bgp^{Cps}}{Cpil} \exp(-Bgp),$$

$$Pnsi = \frac{Bgs^{Csi}}{Csil} \exp(-Bgs), \quad (17)$$

respectively.

Thus, in the case that the p wave and s wave of fluorescence of a light-emitting particle are detected separately, after computing the occurrence probability for every unit time in each of the time series light intensity data of the p wave and s wave with Expression (14) and (17), the occurrence probabilities Pp and Pn in a analysis window with Expression (15) and (16) are computed, and then, by comparing these occurrence probabilities, the presence or absence of a signal of a particle having a fluorescence anisotropy R can be detected. In this regard, in this case, the fluorescence anisotropy R is a known quantity. Thus, for the value of the fluorescence anisotropy R, the value determined experimentally or theoretically by an arbitrary way may be employed. When the value of the fluorescence anisotropy R is computed theoretically, for example, as described in the non-patent document 5, it can be estimated using the molecular weight M of a particle as follows:

$$R = Ro/(1+\tau\theta) \quad (18a)$$

Here, Ro is an anisotropy value when a particle is not moving (=0.3), and $\tau$ is a rotational correlation time. $\theta$ is given by the following expression:

$$\theta = \eta M(V+h)/RoT \quad (18b)$$

Here, $\eta$, V+h, Ro and T are viscosity, hydrated volume, gas constant, and temperature, respectively.

Moreover, according to the manner of detecting a signal of a single particle having a particular fluorescence anisotropy as noted above, in a case that light-emitting particles of two or more kinds having mutually different fluorescence anisotropies are included in a sample solution, it becomes possible to detect a signal of a particle while identifying its kind. Namely, in order to identify the kind of particle, the occurrence probability in assuming that a particle exists as described above for the photon count sequence in each analysis window is computed for each fluorescence anisotropy value. Then, it can be estimated that a particle, possessing the fluorescence anisotropy which gives the highest occurrence probability among the occurrence probabilities acquired with mutually different fluorescence anisotropy values, exists on the currently analyzed photon count sequence.

Figure 4C:
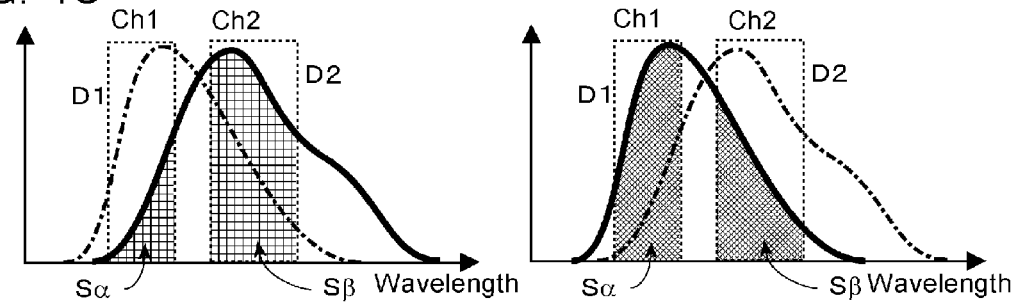

(ii) Detection of a Signal of a Single Particle Possessing a Particular Emission Wavelength Characteristic In detecting the light from a light detection region, when the light components of mutually different wavelength bands are measured separately, the magnitude of the light intensity value of the component of each wavelength band will change depending on the emission wavelength characteristic of a light-emitting particle. For instance, as shown in FIG. 4C, with respect to light-emitting particles D1 and D2 which have mutually different emission wavelength spectrums, when the light components of the wavelength bands, shown by the dotted frames in the drawing, are separately detected as Ch1 and Ch2, respectively, the lights of the respective light-emitting particles detected in the respective Ch1 and Ch2, become the portions overlapping with the detected wavelength bands of Ch1 and Ch2 (the shaped portions) in the emission wavelength spectrums of the corresponding light-emitting particles, so that the light amount of each of them will be the area of the corresponding shaded portions. Therefore, as understood from the drawing, the ratio of the light amounts in Ch1 and Ch2 will change depending on the profile of the emission wavelength spectrum of a light-emitting particle.

The ratio of the light intensities (photon counts) detected in mutually different detected wavelength bands depending on the emission wavelength spectrum of a light-emitting particle as described above is reflected in the photon counts in time series light intensity data obtained by the scanning molecule counting method. Thus, by considering the ratio of photon counts as a predetermined characteristic value in the above-mentioned computation of the occurrence probability of a photon count sequence, it becomes possible to detect selectively a signal of a light-emitting particle possessing a particular emission wavelength characteristic.

Concretely, for a certain light-emitting particle, first, the intensity ratios $\alpha$ and $\beta$ of components of the light detected in the detected wavelength bands Ch1 and Ch2 are given by:

$$\alpha = S\alpha/(S\alpha + S\beta); \quad \beta = S\beta/(S\alpha + S\beta) \quad (19)$$

respectively, $S\alpha$ and $S\beta$ are the integration values (areas) of the emission wavelength spectrum intensity of the light-emitting particle in the detected wavelength bands Ch1 and Ch2, respectively.

With respect to the total of the detected photon counts Ch1 and Ch2, the expected value Epi of the light intensity of each unit time in a certain analysis window when a particle exist is the same as that of Expression (4), and thus, the peak intensity Q is given by:

[Exp. 12]

$$Q = \frac{\sum_{i=0}^{n}(C\alpha i + C\beta i - Bg\alpha - Bg\beta)}{w\sqrt{2\pi}} \quad (20)$$

Here, $C\alpha i$, $C\beta i$, $Bg\alpha$ and $Bg\beta$ are photon counts in Ch1 and Ch2 of each unit time and the intensities of the background light in Ch1 and Ch2, respectively. Thus, the expected values $Ep\alpha$ and $Ep\beta$ of the photon counts in Ch1 and Ch2 are given by:

[Exp. 13]

$$Ep\alpha i = \alpha Q \cdot \exp\left(-\frac{(ti-tc)^2}{2W^2}\right) + Bg\alpha, \quad (21)$$

$$Ep\beta i = \beta Q \cdot \exp\left(-\frac{(ti-tc)^2}{2W^2}\right) + Bg\beta,$$

respectively, and similarly to Expression (1), the occurrence probabilities Ppαi and Ppβi of the detected photon counts in each unit time in Ch1 and Ch2 in assuming that a particle exists each are given by:

[Exp. 14]

$$Pp\alpha i = \frac{Ep\alpha i^{C\alpha i}}{C\alpha i!}\exp(-Ep\alpha i),$$
$$Pp\beta i = \frac{Ep\beta i^{Cp i}}{C\beta i!}\exp(-Ep\beta i)$$
(22)

Therefore, the occurrence probability Pp of the detected photon count sequence in an analysis window in assuming that there exists a light-emitting particle having an emission wavelength characteristic in which the light intensity ratio of Ch1 and Ch2 is α:β is the product of all the occurrence probabilities Ppαi and Ppβi, and thus it is given by:

[Exp. 15]

$$Pp = \prod_{i=0}^{n} Pp\alpha i \times \prod_{i=0}^{n} Pp\beta i = \prod_{i=0}^{n}(Pp\alpha i, Pp\beta i)$$
(23)

On the other hand, when it is assumed that no particles exist, the occurrence probability Pn of the detected photon count sequence in an analysis window becomes:

[Exp. 16]

$$Pn = \prod_{i=0}^{n} Pn\alpha i \times \prod_{i=0}^{n} Pn\beta i = \prod_{i=0}^{n}(Pn\alpha i, Pn\beta i)$$
(24)

Here, Pnαi and Pnβi are the occurrence probabilities in each unit time in the respective components, and thus, similarly to Expression (1), using the background lights Bgα, Bgβ as the expected values, those become:

[Exp. 17]

$$Pn\alpha i = \frac{Bg\alpha^{C\alpha i}}{C\alpha i!}\exp(-Bg\alpha),$$
$$Pn\beta i = \frac{Bg\beta^{Cp i}}{C\beta i!}\exp(-Bg\beta),$$
(25)

respectively.

Thus, in the case that components of mutually different emission wavelength bands of a light-emitting particle is detected separately, after computing the occurrence probabilities for every unit time in each of the time series light intensity data of the respective detected wavelength bands with Expressions (22) and (25), by computing the occurrence probabilities Pp and Pn in an analysis window with Expressions (23) and (24) and comparing them, the presence or absence of a signal of the particle having the particular emission wavelength characteristic can be detected. In this regard, in this case, the ratio of light intensities of Ch1 and Ch2, α:β, is a known quantity. For the value of the intensity ratio, the value determined experimentally or theoretically by an arbitrary way may be employed. Moreover, according to the above-mentioned way, a signal of a particle which having a particular emission wavelength characteristic can be detected selectively, and thus, when light-emitting particles of two or more kinds having mutually different emission wavelength characteristics are included in a sample solution, it becomes possible to detect a signal of a particle while identifying its kind. Namely, in order to identify the kind of particle, the occurrence probability in assuming that a particle exists as described above for the photon count sequence in each analysis window is computed for each ratio of light intensities of Ch1 and Ch2 (α:β). Then, it can be estimated that a particle, possessing the light intensity ratio which gives the highest occurrence probability among the occurrence probabilities acquired with mutually different light intensity ratios, exists on the currently analyzed photon count sequence.

Operation Processes of Scanning Molecule Counting Method

In the embodiment of the scanning molecule counting method in accordance with the present invention with the optical analysis device 1 as illustrated in FIG. 1A, concretely, there are conducted (1) a preparation of a sample solution containing a single particle: (2) a process of measuring the light intensity of the sample solution; and (3) a process of detecting a single particle signal. FIG. 5 shows the processes in this embodiment in form of the flow chart.

(1) Preparation of a Sample Solution

The particle to be an observed object in the inventive optical analysis technique may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological molecules. When the particle to be an observed object is a light-emitting particle and it is originally a particle which emits no light, there is used a particle obtained by attaching a light emitting label (a fluorescence molecule, a phosphorescence molecule, and a chemiluminescent or bioluminescent molecule) to the particle to be the observed object in an arbitrary manner. Typically, the sample solution is an aqueous solution, but not limited to this, and it may be an organic solvent or other arbitrary liquids.

In a case of performing the inverted scanning molecule counting method, while an object to be observed is a non-light-emitting particle, it may be an arbitrary one, similarly in the case of a light-emitting particle. In this connection, it has been found out that a particle diameter is to be preferably not less than 15%, and more preferably not less than 35%, of the diameter of a light detection region. Further, the light-emitting substance which gives the background light may be arbitrary fluorescent molecules, such as fluorescent molecules, phosphorescent molecules, and chemi- and bioluminescent molecules, and the light-emitting substance is dissolved or dispersed in the sample solution at a concentration so that several molecules or more always exist in the light detection region. Typically, the sample solution is an aqueous solution, but not limited to this, and it may be an organic solvent or other arbitrary liquids.

(2) Measurement of Light Intensity of a Sample Solution (FIG. 5—Step 100)

The measurement of the light intensity in the optical analysis by the scanning molecule counting method or the inverted scanning molecule counting method of the present embodiment may be conducted in a manner similar to a measurement process of light intensity in FPCS or FIDA except that the mirror deflector 17 or the stage position changing apparatus 17a is driven to move the position of the light detection region within the sample solution (scanning the sample solution) during the measurement. In the operation processes, typically, after dispensing a sample solution into the well(s) 10 of the micro plate 9 and putting it on the stage of the microscope, when a user inputs to the computer 18 a command of starting a measurement, the computer 18 executes programs memorized in a storage device (not shown) (the process of moving the position of the light detection region in the sample solution, and the process of detecting light from the light detection region during the moving of the position of the light detection region) to start radiating the excitation light and measuring the light intensity in the light detection region. During this measurement, under the control of the operation process of the computer 18 according to the programs, the mirror deflector 17 or the stage position changing apparatus 17a drives the mirror 7 (galvanomirror) or the micro plate 9 on the stage of the microscope to move the position of the light detection region in the well 10, and simultaneously with this, the photodetector 16 sequentially converts the detected light into electric signals and transmits them to the computer 18, which generates the time series light intensity data from the transmitted signals and stores them in an arbitrary manner. In this regard, the photodetector 16 is typically a super high sensitive photodetector which can detect an arrival of a single photon, and thus when the detection of light is performed by the photon counting, the time series light intensity data may be time series photon count data. In addition, in detecting mutually different light components independently, two or more photodetectors 16 each detect simultaneously the light intensity value (photon count) of the corresponding light component, and accordingly, time series light intensity data are generated for each detected mutually different component.

By the way, the moving speed of the position of the light detection region is set preferably to be a value quicker than the moving speed in the random motion, i.e., the Brownian motion of a single particle. If the moving speed of the position of the light detection region is slow in comparison with the moving of the particle owing to the Brownian motion, the particle would move in the light detection region at random. Then, the calculation of the expected value for an occurrence probability in assuming a condition that a particle exists would be complicated, and also, its accuracy could deteriorate. Thus, preferably, the moving speed of the position of the light detection region is set to be quicker than the average moving speed of a particle by the Brownian motion (diffusional moving velocity), so that a particle will pass through the light detection region in an approximately straight line as drawn in FIG. 3C, and thereby the expected value of the profile of the light intensity variation will form a bell-shaped profile similarly to a profile in which the light intensity decreases as the position of the particle becomes more apart from the almost center of a light detection region as drawn in FIG. 3D.

Concretely, the time $\Delta\tau$ required for a single particle having a diffusion coefficient D to pass through the light detection region of radius r (confocal volume) by the Brownian motion is given from the equation of the relation of mean-square displacement:

$$(2r)^2 = 6D \cdot \Delta\tau \quad (26)$$

as:

$$\Delta\tau = (2r)^2/6D \quad (27),$$

and thus, the velocity of the single particle moving by the Brownian motion (diffusional moving velocity) Vdif, becomes approximately $$V\text{dif} = 2r/\Delta\tau = 3D/r \quad (28)$$

Then, with reference to this, the moving speed of the position of the light detection region may be set to a value sufficiently quicker than Vdif. For example, when the diffusion coefficient of a single particle is expected to be about $D=2.0\times10^{-10}$ m²/s, Vdif will be $1.0\times10^{-3}$ m/s, supposing r is about 0.62 μm, and therefore, the moving speed of the position of the light detection region may be set to its 10 times or more, 15 mm/s. In this regard, when the diffusion coefficient of a single particle is unknown, an appropriate moving speed of the position of the light detection region may be determined by repeating the executions of a preliminary experiment with setting various moving speeds of the position of the light detection region in order to find the condition that the profile of the light intensity variation becomes an expected profile (typically, similar to the excitation light intensity distribution).

(3) Individual Detection of a Signal of a Single Particle (Steps 110-160)

When the time series light intensity data is generated, first, the computation of the intensity value of background light is performed on the time series light intensity data (step 110). The intensity value of the background light may be the average of the intensity values (photon counts) in a region where no particle signals exist in the time series light intensity data. Thus, in one way of computing the intensity value of the background light, in a case of the normal scanning molecule counting method (in a case that a particle to be observed is a light-emitting particle), the average of all the intensity values except data of a predetermined proportion (for example, 20%) in the higher side of the light intensity values of the obtained time series light intensity data may be employed as the intensity value of the background light. This is because it is considered that the data of the predetermined proportion in the higher side of the light intensity values would correspond to particle signals. Also, in a case of the inverted scanning molecule counting method (in a case that a particle to be observed is a non light-emitting particle), the average of all the intensity values except data of a predetermined proportion (for example, 20%) in the lower side of the light intensity values of the obtained time series light intensity data may be employed as the intensity value of the background light. This is because it is considered that the data of the predetermined proportion in the lower side of the light intensity values would correspond to particle signals. When time series light intensity data is generated for each of two or more components, the computation of the intensity value of the background light is performed for each component. In this connection, the intensity value of the background light may be the average of the light intensity values on time series light intensity data obtained using a sample solution containing no particles to be observed.

Next, in the process of the present embodiment, the setting of analysis windows is performed on the time series light intensity data (step 120). As already noted, the length of one analysis window may be determined in accordance with the size and the moving speed of the light detection region (See Expression (9)). Further, preferably, an analysis window may be set in time series for every bin time. However, in order to reduce computation amounts, an analysis window may be set for every several bin times, or, analysis windows may also be set without mutually overlapping.

Then, when the setting of the analysis windows has been done, in accordance with the principle explained above, an occurrence probability Pn of the light intensity value sequence or photon count sequence in the analysis window in assuming that no particles exist in the light detection region (step 130), and an occurrence probability Pp of the light intensity value sequence or photon count sequence in the analysis window in assuming that a particle exists in the light detection region (step 140) each are computed: and it is judged whether or not a particle exist in the analysis window (step 150) by comparing the occurrence probability Pn and the occurrence probability Pp. In this judgment, the odds ratio of the occurrence probability Pn and the occurrence probability Pp may be computed (see Expression (8)): and when the odds ratio exceeds beyond a predetermined value, it may be judged that a particle exists. It should be understood that, in a case that time series light intensity data are obtained for two or more mutually different components and the occurrence probability Pp is acquired in consideration of a predetermined characteristic value of a particle, the presence or absence of a signal of a particle which has the predetermined characteristic value is detected selectively.

In this regard, in the computation of the occurrence probability Pp in assuming that a particle exists in the light detection region, the expected value of intensity value may be assumed such that its intensity peak exists at the center of an analysis window. Actually, although, in most cases, the peak of a signal of a particle does not exist at the center of an analysis window and the value of the occurrence probability Pp decreases as the position of the peak of an actual signal of a particle becomes more apart from the center of an analysis window, its value becomes a value higher than the value of the occurrence probability Pp when no actual particle signal exist.

The computation of the occurrence probabilities Pp and Pn in an analysis window and the detection of a particle signal in the processes of the above-mentioned steps 130-150 may be performed in all the analysis windows set out in the light intensity data (Step 160).

(5) Analysis of a Particle Concentration, Etc.

Thus, when the presence or absence of a particle signal in each analysis window is judged through the above-mentioned processes, analyses such as the counting of particle signals on the light intensity data, the computation of their concentration, etc. may be conducted (step 170). As already noted, when the presence or absence of a particle signal in each analysis window is judged, the analysis windows in which one particle signal exists will continue. Therefore, the number of particles will be obtained by counting the sets of continuous analysis windows in which a particle signal exists.

Further, in a case that the number of particles is determined, if the volume of the whole region through which the light detection region has passed is computed out by an arbitrary way, the number density or concentration of the single particle in the sample solution can be determined from the volume and the number of single particles. The volume of the whole region through which the light detection region has passed may be theoretically computed out with the wavelength of excitation light or detected light, the numerical aperture of lenses and the adjustment condition of the optical system. Or, the volume may be determined experimentally, for instance, using the number of single particles detected by performing, with a solution having a known particle concentration (a reference solution), the light intensity measurement, detection of (a) single particle(s) and their counting under the same condition as the measurement of a sample solution to be tested, and the particle concentration of the reference solution. Concretely, for example, supposing the number of detected light-emitting particles is N in a reference solution of the light-emitting particle concentration C, the whole volume Vt of the region through which the light detection region has passed is given by:

$$Vt=N/C \qquad (29).$$

Alternatively, by preparing the plurality of solutions of different particle concentrations and performing the measurement for each of the solutions, the average value of the computed Vts may be employed as the whole volume Vt of the region through which the light detection region has passed. Then, when Vt is given, the concentration c of the particle of the sample solution, whose counting result of the particles is n, is given by:

$$c=n/Vt \qquad (30)$$

In this regard, the volume of the light detection region and the volume of the whole region which the light detection region has passed through may be given by an arbitrary method, for instance, using FCS and FIDA, instead of the above-mentioned method. Further, in the optical analysis device of this embodiment, there may be previously memorized in a storage device of the computer 18 the information on the relations (Expression (29)) between concentrations C and particle numbers N of various standard particles for assumed moving patterns of the light detection region, so that a user of the device can appropriately use the memorized information on the relation in conducting an optical analysis. In this regard, it should be understood that, in a case that time series light intensity data are obtained for several mutually different components and the occurrence probability Pp is acquired in consideration of a predetermined characteristic value of a particle, the counting of signals of particles having the predetermined characteristic value and the computation of their concentration are possible. Therefore, in a case that particles of two or more kinds which have mutually different characteristic values are included in a sample solution, the counting of particles and the computation of their concentrations with identifying the kind of particle are possible for each kind.

In order to verify the validity of the present invention explained above, the experiments described below were conducted. In this regard, it should be understood that the following embodiments illustrate the validity of the present invention only, not intended to limit the scope of the present invention.

Embodiment 1

In the scanning molecule counting method, the detection of particle signals was performed based on occurrence probabilities Pp and Pn of photon count sequences on the time series light intensity data in accordance with the present invention.

For sample solutions, there were prepared solutions containing ATTO647N (Sigma) as light-emitting particles at various concentrations in Tris buffer (including 0.05% Tween20 and 10 mM Tris-HCl (pH 8.0)). In the light measurement, a single molecule fluorescence measuring apparatus MF20 (Olympus Corporation), equipped with the optical system of a confocal fluorescence microscope and a photon counting system, was used as the optical analysis device, and time series light intensity data (photon count data) was acquired for the above-mentioned sample solutions in accordance with the manner explained in the above-mentioned "(2) Measurement of Light Intensity of a Sample Solution".

In the data processing after the light measurement, first, in the acquired time series photon count data, in accordance with the way described in "(3) Individual Detection Of A Signal Of A Single Particle" and steps 110-160 of FIG. 5, the computation of background light intensities: the setting of analysis windows; the computation of an occurrence probability Pn of a photon count sequence in an analysis window in assuming that no particles exist in the light detection region and an occurrence probability Pp of the photon count sequence in the analysis window in assuming that a particle exists in the light detection region; and the computation of an odds ratio of the occurrence probabilities were performed in series, and thus, the signals of single particles were detected and counted. In this regard, in the present embodiment, since time series light intensity data was only for one component of a detected wavelength band, the occurrence probability Pn and the occurrence probability Pp were computed using Expression (1), (2), (6), etc. described in the column of "2. Detection Of A Signal Of A Single particle".

Figure 6A:
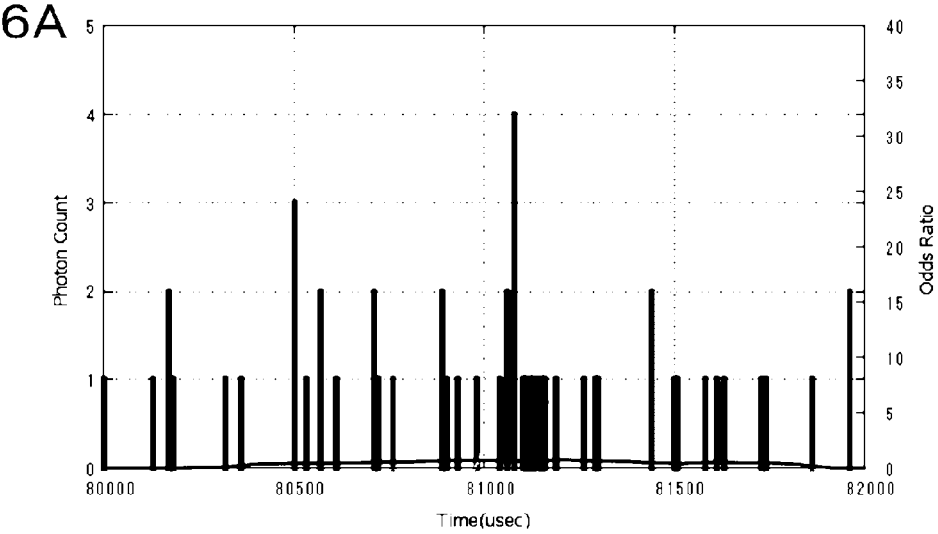
Figure 6B:
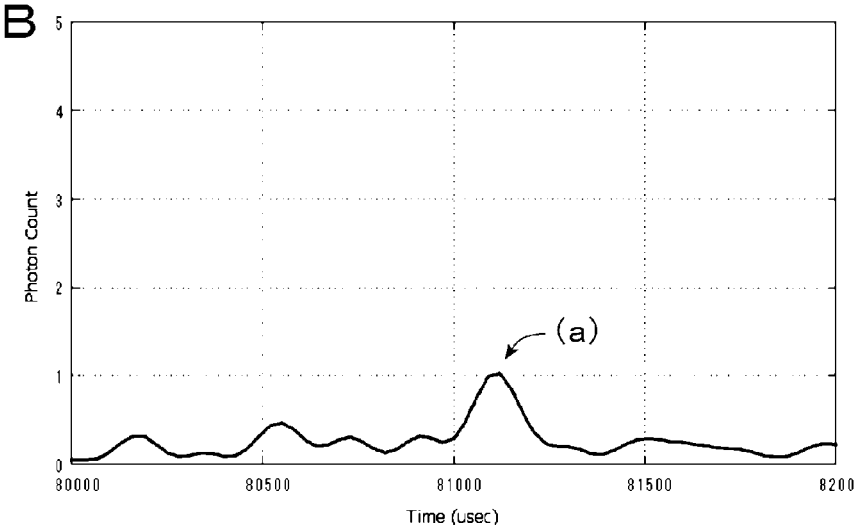
Figure 6C:
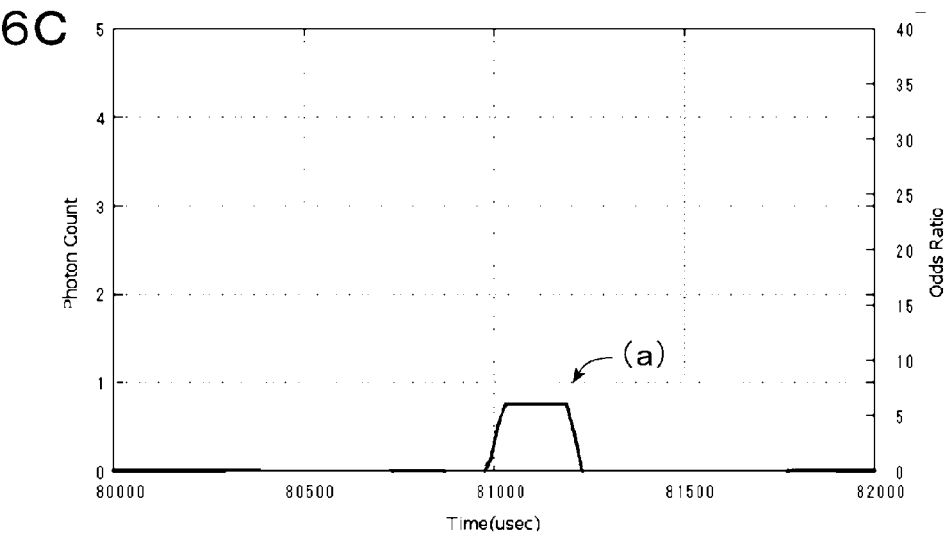

FIG. 6 shows (FIG. 6A) a part of time series light intensity data; (FIG. 6B) data acquired by smoothing (FIG. 6A); and (FIG. 6C) one example of the odds ratio of occurrence probabilities Pn, Pp which were computed from (FIG. 6A) according to the teachings of the present invention. In the acquisition of the data of this drawing, a 633-nm laser light was used for excitation light; the light in the wavelength band of 660 to 710 nm was measured using a band pass filter; and thereby time series photon count data were generated. The moving speed of the position of the light detection region in the sample solution was set to 3000 rpm (7.5 mm/(second)), and BIN TIME was set to 10 μseconds. In the computation of the occurrence probabilities Pn and Pp, the average value of the photon counts of all the data except 20% of the lower side and the higher side of the photon counts in the photon counts of all data in the time region of 1 m-second shown in the drawing was used for the intensity of the background light. In the computation of the expected value of photon count in assuming that a particles exists, the full width at half maximum (d/v) of the Gauss function (Expression (4)) indicating the distribution of the expected value was set to 80 μseconds. Further, the time width of an analysis window was set to 300 μseconds. And, the concentration of ATTO647N in the sample solution was prepared at 1 pM.

Referring to FIGS. 6A-6C, in the data of FIG. 6B acquired by the smoothing, whether or not a signal is a particle signal is judged by judging whether or not the intensity of the pulse form signal exceeds beyond a predetermined threshold value through the judgment process for a particle signal to judge the magnitude of the signal intensity in the smoothed data with reference to the predetermined threshold value as described in patent documents 9-11. Since the predetermined threshold value is typically set to 1 photon count, all the data will be judged as noise except the increase of photon counts around the center in the drawing indicated with (a). Although the peak value of the pulse form signal indicated with (a) is ~1 photon count so that it can be considered to be a particle signal, the judgment result could be changed by the influence of error, and thus, it would be possible that it could be judged as a noise signal (namely, the result is unstable.).

On the other hand, in the odds ratio (FIG. 6C) of the occurrence probabilities Pn and Pp, a remarkable increase of the value is seen in the region corresponding to the signal indicated with (a), and therefore, it can be stably judged as a particle signal.

Figure 7A:
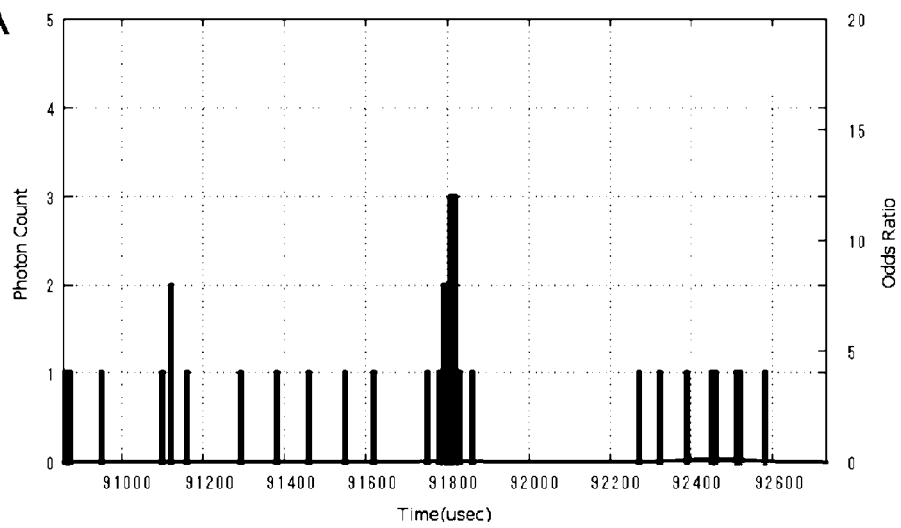
FIGS. 7A-7C is figures similar to FIGS. 6A-6C, showing a different part of the time series light intensity data.
Figure 7B:
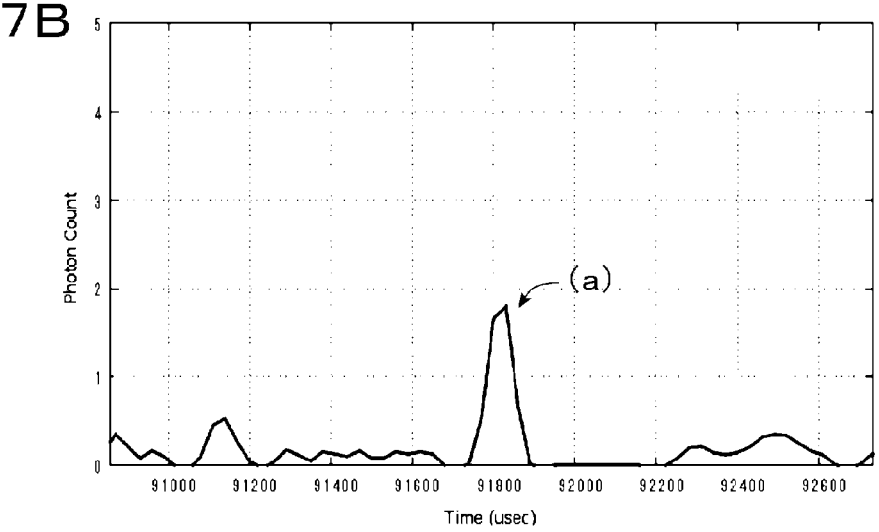
Figure 7C:
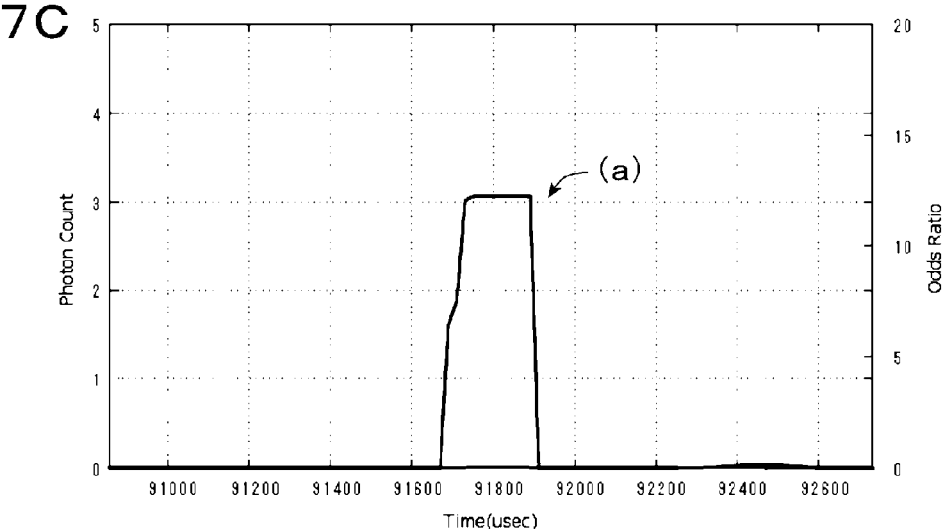

FIGS. 7A-7C is a drawing showing another part of the time series light intensity data similar to FIGS. 6A-6C. In the acquisition of the data of this drawing, the moving speed of the position of the light detection region in the sample solution was set to 6000 rpm (15 mm/sec.). With reference to FIG. 7A-7C, while a significant pulse form signal was observed besides the pulse form signal indicated with (a) in the data of FIG. 7B acquired by the smoothing, no significant increase was seen other than the region corresponding to the pulse form signal indicated with (a) in the odds ratio (FIG. 7C) of the occurrence probabilities Pn and Pp. This suggests that, according to the judgment based on the occurrence probabilities Pn and Pp computed in accordance with the teachings of the present invention, the discrimination between a particle signal and a noise signal becomes clearer, and the stability of the particle judgment is improved.

Figure 8:
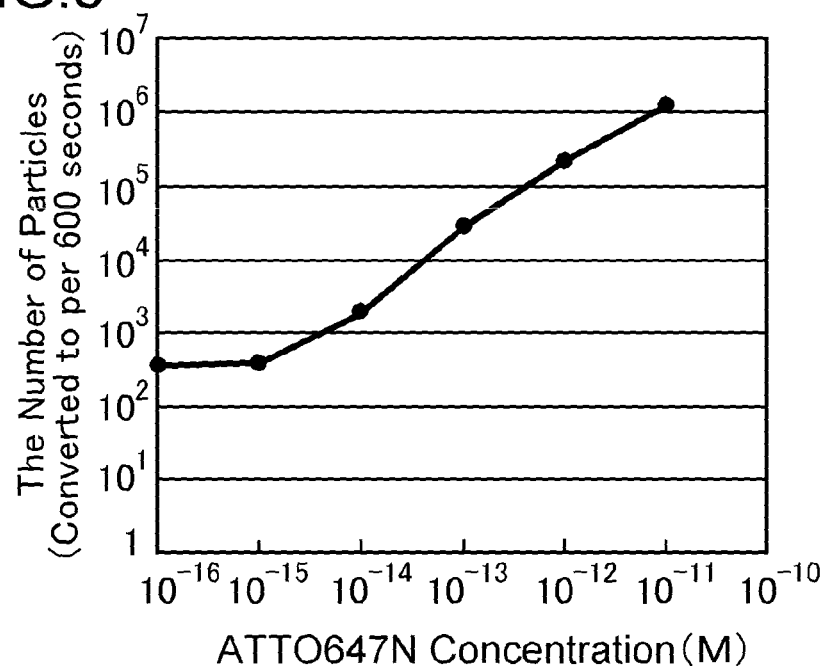
FIG. 8 is a diagram showing a relation between light-emitting particle (ATTO647N) concentrations in sample solutions and the number of detected particles in a case that detection and counting of light-emitting particles were performed by the scanning molecule counting method in accordance with the present invention.

FIG. 8 shows a relation between light-emitting particle concentrations and the numbers of detected particles in a case that the judgment of particle signals, using the odds ratio of the occurrence probabilities Pn and Pp, for sample solutions containing various concentrations of light-emitting particle. In this regard, in this experiment, a 642-nm laser light (3 mW) was used for excitation light; and the light of the wavelength band of 560 to 620 nm was measured using a band pass filter, and thereby time series photon count data were generated. The moving speed of the position of the light detection region in the sample solution was set to 12000 rpm (90 mm/sec.); the BIN TIME was set to 10 μseconds: and the measuring time of the light was 600 seconds. In the computation of the occurrence probabilities Pn and Pp, for the intensity of the background light, the average value of the photon counts of all the data except 20% of the lower and higher sides of photon counts in the data of 1 m second around each analysis window was used. In the computation of the expected value of the photon count in assuming that a particle exists, the full width at half maximum (d/v) of the Gauss function (Expression (4)) indicating the distribution of the expected value was set to 50 μseconds. Further, the time width of an analysis window was set to 350 μseconds. And, it was judged that a particle signal exists in a region in which odds ratio>$10^8$ was established. As understood from FIG. 8, the detected particle count increased with the light-emitting particle concentration in the concentration range of 1 fM or more. This shows that a signal of a particle on time series photon count data can be detected by the inventive method of detecting a particle signal, and that the particle concentration in a sample solution can be determined in the concentration range of 1 fM or more.

Embodiment 2

In the inverted scanning molecule counting method, the detection of particle signals was performed based on occurrence probabilities Pp and Pn of photon count sequences on the time series light intensity data in accordance with the present invention.

For sample solutions, there were solutions in which polystyrene beads (4 μmeters in diameter) were dispersed in Tris buffer (including 0.06% Tween 20 and 10 mM Tris-HCl (pH 8.0)) which contained 1 mM ATTO647N as light-emitting substance generating background light. In the light measurement, a single molecule fluorescence measuring apparatus MF20 (Olympus Corporation), equipped with the optical system of a confocal fluorescence microscope and a photon counting system, was used as the optical analysis device, and time series light intensity data (photon count data) was acquired for the above-mentioned sample solutions in accordance with the manner explained in the above-mentioned "(2) Measurement of Light Intensity of a Sample Solution".

In the data processing after the light measurement, first, in the acquired time series photon count data, in accordance with the way described in "(3) Individual Detection Of A Signal Of A Single Particle" and steps 110-160 of FIG. 5, the computation of background light intensities; the setting of analysis windows; the computation of an occurrence probability Pn of a photon count sequence in an analysis window in assuming that no particles exist in the light detection region and an occurrence probability Pp of the photon count sequence in the analysis window in assuming that a particle exists in the light detection region; and the computation of an odds ratio of the occurrence probabilities were performed in series, and thus, the signals of single particles were detected and counted. In this regard, in the present embodiment, since time series light intensity data is only for one component of a detected wavelength band, the occurrence probability Pn and the occurrence probability Pp were computed using Expression (1), (2), (6), etc. described in the column of "2. Detection Of A Signal Of A Single particle".

FIGS. 9A, 9B and FIG. 10 show drawings of parts of obtained time series light intensity data (upper row) and their odds ratios being enlarged successively. In the acquisition of the data of these drawings, a 633-nm laser light (50 μW) was used for excitation light; the light in the wavelength band of 660 to 710 nm was measured using a band pass filter; and thereby time series photon count data were generated. The moving speed of the position of the light detection region in the sample solution was set to 6000 rpm (15 mm/sec.), and BIN TIME was set to 50 μseconds. In the computation of the occurrence probabilities Pn and Pp, for the intensity of the background light, the average value of the photon counts of all the data except 20% of the lower and higher sides of photon counts in the data of 1 m second around each analysis window was used. In the computation of the expected value of the photon count in assuming that a particle exists, the full width at half maximum (d/v) of the Gauss function (Expression (4)) indicating the distribution of the expected value was set to 100 μseconds. Further, the time width of an analysis window was set to 300 μseconds. The bead concentration was prepared at 100 fM.

With reference to these drawings, it can be understood that an increase of odds ratio corresponds with a reduction part of the background light on the photon count data. Thereby, it is suggested that the way of the inventive particle signal detection can be applied also to the inverted scanning molecule counting method.

FIG. 11A shows a relation between particle concentrations and the numbers of detected particles in a case that the judgment of particle signals, using the odds ratio of the occurrence probabilities Pn and Pp, for sample solutions containing the beads at various concentrations. In this regard, in this experiment, a 633-nm laser light (50 μW) was used for excitation light; and the light of the wavelength band of 660 to 710 nm was measured using a band pass filter, and thereby time series photon count data were generated. The moving speed of the position of the light detection region in the sample solution was set to 9000 rpm (90 mm/sec.); the BIN TIME was set to 10 μseconds; and the measuring time of the light was 200 seconds. In the computation of the occurrence probabilities Pn and Pp, for the intensity of the background light, the average value of the photon counts of all the data except 20% of the lower and higher sides of photon counts in the data of 1 m second around each analysis window was used. In the computation of the expected value of the photon count in assuming that a particle exists, the full width at half maximum (d/v) of the Gauss function (Expression (4)) indicating the distribution of the expected value was set to 100 μseconds. Further, the time width of an analysis window was set to 300 μseconds. And, it was judged that a particle signal exists in a region in which odds ratio>$10^{10}$ was established. In this regard, for a comparison, FIG. 11B shows a relation between the numbers of the detected particles obtained by carrying out the fitting of the Gauss function and detecting a pulse form signal of peak photon count ≥5 after smoothing time series photon count data and the particle concentrations for the same data.

Referring to FIGS. 11A and 11B, in the concentration range (1 aM-1 fM) shown in the drawings, in the case of the results (FIG. 11B) obtained by carrying out the fitting of the Gauss function in the smoothed time series photon count data, although the increase of the number of the detected particles was observed with the increase of the concentrations, the dispersion was comparatively large (the correlation coefficient of the approximate line $r^2$=0.93). On the other hand, in the results of FIG. 11A according to the inventive detection method of a particle signal, the number of the detected particles was generally proportional to the particle concentration (the correlation coefficient of the approximate line $r^2$=0.99). In addition, from this drawing, it is shown that the particle concentration in a sample solution can be determined in the concentration range of 50 aM or more (The concentration range which can be determined in FIG. 11B is 500 aM or more.).

Embodiment 3

It was verified that, for light-emitting particles of two kinds having different fluorescence anisotropies, the detection of particles was possible by the kind in accordance with the inventive scanning molecule counting method.

For sample solutions, there were prepared a solution containing a fluorescent dye TAMRA (M. W.430.45 Sigma-Aldrich Cat. No. C2734) at 100 fM in a phosphate buffer (containing 0.05% Tween20) (Fluorescent dye solution) and a solution containing plasmid (pbr322, 2.9MDa, Takara Bio, Inc. Cat. No. 3035) at 1 pM and DNA intercalator fluorescent dye SYTOX Orange (Invitrogen Corp. Cat. No. S-11368) at 10 nM in the phosphate buffer (Plasmid solution, SYTOX Orange binds with a single plasmid to form a single light-emitting particle.). In the light measurement, a single molecule fluorescence measuring apparatus MF20 (Olympus Corporation), equipped with the optical system of a confocal fluorescence microscope and a photon counting system, was used as the optical analysis device, and time series light intensity data (photon count data) of s polarized light component and p polarized light component were simultaneously and separately acquired for the above-mentioned sample solutions in accordance with the manner explained in the above-mentioned "(2) Measurement of Light Intensity of a Sample Solution". In that time, for both the TAMRA solution and the plasmid solution, a 543-nm laser light was used for excitation light, and, using a band pass filter, the light of the wavelength band, 560 to 620 nm, was detected. Further, the polarization direction of the excitation light was set to be the same direction as p polarized light component of the detected light. The moving speed of the light detection region in the sample solution was set to 6000 rpm (15 mm/sec); BIN TIME, 10 μsec., and the measurement time was set to 2 seconds. For the above-mentioned sample solutions, time series light intensity data (photon count data) were acquired.

In the data processing after the light measurement, first, in the acquired time series photon count data, in accordance with the way described in "(3) Individual Detection Of A Signal Of A Single Particle" and steps 110-160 of FIG. 5, the computation of background light intensities: the setting of analysis windows; the computation of an occurrence probability Pn of a photon count sequence in an analysis window in assuming that no particles exist in the light detection region and an occurrence probability Pp of the photon count sequence in the analysis window in assuming that a particle exists in the light detection region; and the computation of an odds ratio of the occurrence probabilities were performed in series, and thus, the signals of single particles were detected and counted. In this regard, in the present embodiment, the occurrence probabilities Pn and occurrence probabilities Pp, comprising fluorescence anisotropy as a known parameter, were computed from the time series light intensity data of two components, p wave and s wave, using Expressions (15), (16), etc. described in the columns of "3. Detection of Single Particle Signal Using Measurement of Two or More Light Components, (i) Detection of a signal of a single particle possessing a particular polarization characteristic". In that case, for the intensity of the background light, the average value of the photon counts of all the data except 20% of the lower and higher aides of photon counts in the data of 1 m second around each analysis window was used. In the computation of the expected value of the photon count in assuming that a particle exists, the full width at half maximum (d/v) of the Gauss function (Expression (4)) indicating the distribution of the expected value was set to 120 μseconds. Further, the time width of an analysis window was set to 400 μseconds. In addition, with respect to the occurrence probabilities Pp, the value with 0.4 of the fluorescence anisotropy of the plasmid and the value with 0.32 of the fluorescence anisotropy of TAMRA were computed (Namely, two occurrence probabilities Pp were computed for one analysis window.), and for each of them, when the odds ratio with the occurrence probability Pn exceeded beyond 20, it was judged that a signal of a particle of the corresponding kind existed in the analysis window (When both the odds ratio of the occurrence probability Pp of the plasmid and the odds ratio of the occurrence probability Pp of TAMRA exceeded beyond 20, it was judged that the particle signal of the kind of the higher odds ratio existed.).

FIG. 12 shows results of the counting of the number of particles for the respective kinds of particle by judging an existence of a particle signal with the odds ratios of the occurrence probability Pn and the occurrence probabilities Pp obtained using mutually different fluorescence anisotropies in the time series light intensity data obtained by the above-mentioned scanning molecule counting method for the plasmid solution and the fluorescent dye solution. Referring to the drawing, as understood from it, for each of the solutions, most particle signals were detected as a particle of the corresponding kind (In the plasmid solution, 421 particle signals were detected, in which the number of signals erroneously detected as TAMRA was 82. On the other hand, in the fluorescent dye solution, 279 particle signals were detected, in which the number of signals erroneously detected as plasmid was 58.). This result suggests that, in accordance with the way of the present invention, the detection of a single particle in a sample solution is possible with identifying its kind.

Thus, as understood from the results of the above-mentioned embodiments, it has been shown that, in accordance with the teachings of the present invention, by computing occurrence probabilities of light intensity value sequence in time series light intensity data for each of the case of assuming that a particle exists and the case of assuming that no particle exist in the scanning molecule counting method and judging the presence or absence of a signal of a particle based on the computed occurrence probabilities, the accuracy or the S/N ratio in the detecting of a signal of a particle is improved and the detection sensitivity (the range of the particle concentration of a sample solution in which a signal of a particle is detectable at allowable accuracy) can be improved.

The invention claimed is:

1. An optical analysis device which detects a single particle dispersed and moving at random in a sample solution using an optical system of a confocal microscope or a multiphoton microscope, comprising:
   a light detection region mover which moves a position of a light detection region of the optical system in the sample solution;
   a light detector which detects light from the light detection region; and
   a signal processor which generates time series light intensity data of the light from the light detection region detected with the light detector during the moving of the position of the light detection region in the sample solution and detects a signal indicating an existence of each single particle individually in the time series light intensity data;
   wherein the signal processor computes a first occurrence probability in assuming a first condition that no single particles exist in the light detection region and a second occurrence probability in assuming a second condition that a single particle exists in the light detection region for a time variation of light intensity value in each analysis window set out in time series on the time series light intensity data; and detects a signal indicating an existence of each single particle on the time series light intensity data based on the first and second occurrence probabilities.

2. The device of claim 1, wherein the single particle has a predetermined characteristic value; the light detector detects separately at least two mutually different components of the light from the light detection region; the signal processor generates time series light intensity data of each of the components; the signal processor further computes the first and second occurrence probabilities of each of the components; the second occurrence probability of each of the components is a function of the predetermined characteristic value; and a signal indicating an existence of the single particle having the predetermined characteristic value on the time series light intensity data is detected based on the first and second occurrence probabilities of each of the components.

3. The device of claim 2, wherein the single particles include single particles of two or more kinds which have mutually different predetermined characteristic values; the second occurrence probability of each of the components which is a function of the mutually different predetermined characteristic value is computed for each of the kinds of the single particles; a signal indicating an existence of the single particle on the time series light intensity data is detected for each of the kinds of the single particles based on the first occurrence probability of each of the components and the second occurrence probability of each of the components for each of the two or more kinds of the single particles.

4. The device of claim 2, wherein the single particle is a light-emitting particle; the signal indicating an existence of each single particle is a temporary increase of the light intensity; and the predetermined characteristic value is a polarization anisotropy of the single particle.

5. The device of claim 2, wherein the single particle is a light-emitting particle; the signal indicating an existence of each single particle is a temporary increase of the light intensity; and the predetermined characteristic value is a ratio of emitted light intensities in mutually different emission wavelength bands of the single particle.

6. The device of claim 1, wherein the single particle is a non light-emitting particle; the light from the light detection region includes background light; and the signal indicating an existence of each single particle is a temporary reduction of the light intensity from the background light.

7. An optical analysis method of detecting a single particle dispersed and moving at random in a sample solution using an optical system of a confocal microscope or a multiphoton microscope, comprising steps of:
moving a position of a light detection region of the optical system in the sample solution;
detecting light from the light detection region during the moving of the light detection region in the sample solution to generate time series light intensity data;
computing a first occurrence probability in assuming a first condition that no single particles exist in the light detection region and a second occurrence probability in assuming a second condition that a single particle exists in the light detection region for a time variation of light intensity value in each analysis window set out in time series on the time series light intensity data; and
detecting a signal indicating an existence of each single particle on the time series light intensity data based on the first and second occurrence probabilities.

8. The method of claim 7, wherein the first and second occurrence probabilities are computed based upon a light intensity value in each unit time in the analysis window and an expected value in each unit time in assuming the first and second conditions, respectively.

9. The method of claim 8, wherein an unit time occurrence probability of the light intensity value in each unit time is computed under an assumption that the light intensity value in each unit time follows Poisson distribution having the expected value in the each unit time, and the first and second occurrence probabilities are computed using the corresponding unit time occurrence probabilities, respectively.

10. The method of claim 7, wherein the single particle has a predetermined characteristic value; at least two mutually different components of the light from the light detection region are detected separately; time series light intensity data of each of the components are generated; the first and second occurrence probabilities of each of the components are further computed; the second occurrence probability of each of the components is a function of the predetermined characteristic value; and a signal indicating an existence of the single particle having the predetermined characteristic value on the time series light intensity data is detected based on the first and second occurrence probabilities of each of the components.

11. The method of claim 10, wherein the single particles include single particles of two or more kinds which have mutually different predetermined characteristic values; the second occurrence probability of each of the components which is a function of the mutually different predetermined characteristic value is computed for each of the kinds of the single particles; a signal indicating an existence of the single particle on the time series light intensity data is detected for each of the kinds of the single particles based on the first occurrence probability of each of the components and the second occurrence probability of each of the components for each of the two or more kinds of the single particles.

12. The method of claim 10, wherein the single particle is a light-emitting particle; the signal indicating an existence of each single particle is a temporary increase of the light intensity; and the predetermined characteristic value is a polarization anisotropy of the single particle.

13. The method of claim 10, wherein the single particle is a light-emitting particle; and the signal indicating an existence of each single particle is a temporary increase of the light intensity; the predetermined characteristic value is a ratio of emitted light intensities in mutually different emission wavelength bands of the single particle.

14. The method of claim 7, wherein the single particle is a non light-emitting particle; the light from the light detection region includes background light; and the signal indicating an existence of each single particle is a temporary reduction of the light intensity from the background light.

15. A non-transitory computer readable storage device having a computer program product including programmed instructions for optical analysis of detecting light from a light-emitting particle dispersed and moving at random in a sample solution using an optical system of a confocal microscope or a multiphoton microscope, said programmed instructions causing a computer to perform steps comprising:
moving a position of a light detection region of the optical system in the sample solution;
detecting light from the light detection region during the moving of the light detection region in the sample solution to generate time series light intensity data;
computing a first occurrence probability in assuming a first condition that no single particles exist in the light detection region and a second occurrence probability in assuming a second condition that a single particle exists in the light detection region for a time variation of light intensity value in each analysis window set out in time series on the time series light intensity data; and
detecting a signal indicating an existence of each single particle on the time series light intensity data based on the first and second occurrence probabilities.

16. The non-transitory computer readable storage device of claim 15, wherein the single particle has a predetermined characteristic value; at least two mutually different components of the light from the light detection region are detected separately; time series light intensity data of each of the components are generated; the first and second occurrence probabilities of each of the components are further computed; the second occurrence probability of each of the components is a function of the predetermined characteristic value; and a signal indicating an existence of the single particle having the predetermined characteristic value on the time series light intensity data is detected based on the first and second occurrence probabilities of each of the components.

17. The non-transitory computer readable storage device of claim 16, wherein the single particles include single particles of two or more kinds which have mutually different predetermined characteristic values; the second occurrence probability of each of the components which is a function of the mutually different predetermined characteristic value is computed for each of the kinds of the single particles; a signal indicating an existence of the single particle on the time series light intensity data is detected for each of the kinds of the single particles based on the first occurrence probability of each of the components and the second occurrence probability of each of the components for each of the two or more kinds of the single particles.

18. The non-transitory computer readable storage device of claim 16, wherein the single particle is a light-emitting particle; the signal indicating an existence of each single particle is a temporary increase of the light intensity; and the predetermined characteristic value is a polarization anisotropy of the single particle.

19. The non-transitory computer readable storage device of claim 16, wherein the single particle is a light-emitting particle; the signal indicating an existence of each single particle is a temporary increase of the light intensity; and the predetermined characteristic value is a ratio of emitted light intensities in mutually different emission wavelength bands of the single particle.

20. The non-transitory computer readable storage device of claim 15, wherein the single particle is a non light-emitting particle; the light from the light detection region includes background light; and the signal indicating an existence of each single particle is a temporary reduction of the light intensity from the background light.

* * * * *